US012338461B2

(12) United States Patent
Yan et al.

(10) Patent No.: US 12,338,461 B2
(45) Date of Patent: Jun. 24, 2025

(54) THREE-DIMENSIONAL CULTURE METHOD FOR LARGE-SCALE PREPARATION OF STEM CELLS

(71) Applicant: Beijing CytoNiche Biotechnology Co., Ltd., Beijing (CN)

(72) Inventors: Xiaojun Yan, Beijing (CN); Wei Liu, Beijing (CN); Kun Zhang, Beijing (CN)

(73) Assignee: Beijing CytoNiche Biotechnology Co., Ltd., Beijing (CN)

( * ) Notice: Subject to any disclaimer, the term of this patent is extended or adjusted under 35 U.S.C. 154(b) by 997 days.

(21) Appl. No.: 17/310,418

(22) PCT Filed: Oct. 14, 2019

(86) PCT No.: PCT/CN2019/110956
§ 371 (c)(1),
(2) Date: Feb. 3, 2022

(87) PCT Pub. No.: WO2020/155668
PCT Pub. Date: Aug. 6, 2020

(65) Prior Publication Data
US 2022/0162560 A1 May 26, 2022

(30) Foreign Application Priority Data

| Jan. 31, 2019 | (CN) | 201910097650.5 |
| Jan. 31, 2019 | (CN) | 201910098003.6 |
| Jan. 31, 2019 | (CN) | 201910101736.0 |
| Jun. 3, 2019 | (CN) | 201910476110.8 |
| Jun. 12, 2019 | (CN) | 201910505614.8 |
| Aug. 30, 2019 | (CN) | 201910812773.2 |

(51) Int. Cl.
| C12N 5/00 | (2006.01) |
| A01N 1/02 | (2006.01) |
| A01N 1/122 | (2025.01) |
| A01N 1/162 | (2025.01) |
| C12M 1/34 | (2006.01) |
| C12N 5/0775 | (2010.01) |
| C12Q 1/06 | (2006.01) |
| G01N 15/1434 | (2024.01) |
| G01N 15/01 | (2024.01) |
| G01N 15/10 | (2006.01) |
| G01N 15/14 | (2006.01) |

(52) U.S. Cl.
CPC .......... *C12N 5/0667* (2013.01); *A01N 1/122* (2025.01); *A01N 1/162* (2025.01); *G01N 15/1434* (2013.01); *C12N 2511/00* (2013.01); *C12N 2513/00* (2013.01); *C12N 2523/00* (2013.01); *C12N 2527/00* (2013.01); *C12N 2531/00* (2013.01); *G01N 15/01* (2024.01); *G01N 2015/1006* (2013.01); *G01N 2015/1486* (2013.01)

(58) Field of Classification Search
None
See application file for complete search history.

(56) References Cited

U.S. PATENT DOCUMENTS

| 9,102,915 B2 | 8/2015 | Harmon et al. |
| 2008/0118561 A1 | 5/2008 | Nugent et al. |
| 2012/0219531 A1 | 8/2012 | Oh et al. |
| 2018/0216072 A1 | 8/2018 | Lock et al. |

FOREIGN PATENT DOCUMENTS

| CN | 109566604 A | 4/2019 |
| CN | 109593704 A | 4/2019 |
| CN | 109628373 A | 4/2019 |
| CN | 110218764 A | 9/2019 |
| CN | 110229782 A | 9/2019 |
| CN | 110218764 B | 1/2021 |
| JP | 2008532565 A | 8/2008 |
| JP | 2009517072 A | 4/2009 |
| JP | 2011514169 A | 5/2012 |

OTHER PUBLICATIONS

Fernandes, AM; et al; "Mouse embryonic stem cell expansion in a microcarrier-based stirred culture system" Journal of Biotechnology, 132, 227-236, 2007 (Year: 2007).*
Gemma Eibes et al: "Maximizing the ex vivo expansion of human mesenchymal stem cells using a microcarrier-based stirred culture system", Journal of Biotechnology, vol. 146, No. 4, Apr. 15, 2010 (Apr. 15, 2010), pp. 194-197, XP0055063966.
Rafiq Qasim A. et al: "Systematic microcarrier screening and agitated culture conditions improves human mesenchymal stem cell yield in bioreactors", Biotechnology Journal, vol. 11, No. 4, Apr. 1, 2016 (Apr. 1, 2016), pp. 473-486, XP0055837140.
Francisco Dos Santos et al: "Toward a Clinical-Grade Expansion of Mesenchymal Stem Cells from Human Sources: A Microcarrier-Based Culture System Under Xena-Free Conditions", Tissue Engineering Part C: Methods, vol. 17, No. 12, Dec. 1, 2011 (Dec. 1, 2011), pp. 1201-1210, XP0055064158.
Goh Tony Kwang-Poh et al: "Microcarrier Culture for Efficient Expansion and Osteogenic Differentiation of Human Fetal Mesenchymal Stem Cells", BioResearch open access, vol. 2, No. 2, Apr. 1, 2013 (Apr. 1, 2013), pp. 84-97, XP0055776855.
Yan Xiaojun et al: "Dispersible and Dissolvable Porous Microcarrier Tablets Enable Efficient Large-Scale Human Mesenchymal Stem Cell Expansion", Tissue Engineering. Part C, Methods Dec. 2008, vol. 26, No. 5, May 1, 2020 (May 1, 2020), pp. 263-275, XP0055877706.

(Continued)

Primary Examiner — David W Berke-Schlessel
(74) Attorney, Agent, or Firm — LKGlobal | Lorenz & Kopf, LLP

(57) ABSTRACT

A three-dimensional culture method for large-scale preparation of stem cells, comprising a three-dimensional microcarrier-based cell resuscitation method, a three-dimensional microcarrier cell culture-based in situ passage method, a three-dimensional microcarrier in situ freeze preservation method for cells, a three-dimensional microcarrier cell adsorption culture method, a method for harvesting cells on a three-dimensional microcarrier, a method for sampling cells cultured on a microcarrier, and a three-dimensional microcarrier-based cell large-scale expansion method.

20 Claims, 16 Drawing Sheets

(56) References Cited

OTHER PUBLICATIONS

Rodrigues, Andre Lopes, "Scalable expansion and harvesting of hiPSCs using dissolvable microcarriers", Oct. 1, 2017 (Oct. 1, 2017), XP055726537, Retrieved from the Internet: URL:https://fenix.tecnico.ulisboa.pt/downloadFile/1689244997257906/Master%20thesis_Andre%20Rodrigues_fenix_tinal_version%20. pdf.
Shyu, John, et al: "Cell Expansion with Dissolvable Microcarriers", Mar. 1, 2018 (Mar. 1, 2018), XP093076392, Retrieved from the Internet: URL:https://www.corning.com/media/cn/cls/documents/DMC/Cell%20Expansion%20with%20Dissolvable%20Microcarriers.pdf.
Nie, Y. et al. "Scalable Culture and Cryopreservation of Human Embryonic Stem Cells on Microcarriers", Biotechnology Progress, American Chemical Society, Feb. 5, 2009, pp. 20-31, vol. 25, No. 1.
Takahashi, I. et al. "Effects of agitation rate on aggregation during beads-to-beads subcultivation of microcarrier culture of human mesenchymal stem cells", Cytotechnology, Springer Netherlands, Dordrecht, Jun. 28, 2016, pp. 503-509, vol. 69, No. 3.
EPO, Supplementary European Search Report issued in EP Application No. 19912906.5, dated Oct. 10, 2022.
CNIPA, International Search Report issued in International App. No. PCT/CN2019/110956, dated Jan. 21 200.

\* cited by examiner

Before Cryopreservation

After Cryopreservation

THREE-DIMENSIONAL CULTURE METHOD FOR LARGE-SCALE PREPARATION OF STEM CELLS

FIELD OF THE INVENTION

The present invention relates to the field of cell culture, in particular to a three-dimensional (3D) culture method for large-scale preparation of stem cells.

BACKGROUND OF THE INVENTION

Stem cells are a class of multipotent cells with the ability to self-replicate and, after induction under appropriate conditions, can differentiate into a variety of functional cells, such as neuronal cells, cardiomyocytes, vascular endothelial cells, renal cells and hepatocytes. With the development of stem cell research, the medical value of stem cells is immeasurable and the potential for clinical application has a huge impact on the development of medicine. Stem cells, as well as their secretions, have been proven in several studies to play a role in the treatment of a variety of diseases such as tumors, spinal cord injury, multiple sclerosis, stroke, amyotrophic lateral sclerosis, Alzheimer's disease, osteoarthritis, femoral head necrosis, disc degeneration, myocardial infarction, cirrhosis, Crohn's disease, interstitial lung disease, systemic lupus erythematosus, erectile dysfunction, and premature ovarian failure. Stem cells that can be used in regenerative medicine include, but are not limited to, mesenchymal stem cell (MSC), embryonic stem cell (ESC), adipocyte stem cell (ADSC), neural stem cell (NSC), induced pluripotent stem cell (iPSC), and the like of various tissue sources, of which MSC is the most clinically used.

Stem cells are considered as "drugs" for management and approval in many countries around the world. There are currently 14 stem cell therapy products available internationally, while there are still no approved products in China. However, since 2018, when China's stem cell products began to be regulated according to drug supervision and management, several stem cell drugs have been accepted by the National Medical Products Administration (NMPA), and three of them have been approved by IND to enter clinical trials. At the same time, 51 stem cell clinical studies have been filed with the National Health Commission, and allowed to conduct clinical studies. These figures mean that China will enter a rapid development stage of stem cell drug development and translation. These figures imply that China will enter a rapid development stage of stem cell drug development and transformation.

Stem cells and the cellular products derived from them have long been considered difficult to become drugs due to their special properties such as heterogeneity and changes in activity. Compared with traditional "chemical drugs" and "protein, nucleic acid" and other biological drugs, the production and preparation of emerging cellular drugs are more complex and difficult. However, at present, the production process of both foreign marketed stem cell products and domestic clinical trials or research stem cell products still mainly relies on the traditional two-dimensional preparation process of artificial culture. The preparation method relies on a large number of manual operations, cumbersome steps, and an overly labor-intensive open-ended process that makes it difficult to standardize operations and to produce large quantities of cells needed to meet the needs of various cell therapies. In addition to the high cost and the large area of production space required, the limited number of batches of cell products produced and the safety issues caused by the unstable quality of stem cells from batch to batch due to uncertainties and uncontrollable factors in each process all bring into question the possibility of stem cells becoming a drug for large-scale application. Looking ahead, therefore, when cells are formulated into marketable commercial products, the scale may require a cell count of $10^{11}$ cells or more in the same production batch, especially when the cell product requires multiple high doses to achieve a therapeutic effect, such a quantity cannot be delivered consistently and in a timely manner by existing production processes. Therefore, there is an urgent need to establish a method that can simplify the operation, reduce manual handling, and enable closed or semi-closed large-scale culture of stem cells as a key factor to drive the stem cell therapy industry and make clinical-grade stem cell preparation possible.

SUMMARY OF THE INVENTION

The present invention provides a three-dimensional culture method for large-scale preparation of stem cells.

The present invention provides a set of three-dimensional microcarrier-based cell culture methods, including a three-dimensional microcarrier-based cell recovery method, a three-dimensional microcarrier cell culture-based in situ passaging method, and a three-dimensional microcarrier-based in situ cell cryopreservation method;

The three-dimensional microcarrier-based cell recovery method comprises the following steps: inoculating a cell suspension of cryopreserved cells or cryopreserved cell microtissues after thawing onto a three-dimensional microcarrier for cell recovery and culture;

The three-dimensional microcarrier cell culture-based in situ passaging method comprises the following steps: inserting seed microcarriers into new microcarriers; the seed microcarrier is a microcarrier for culturing cells to be passaged; and The three-dimensional microcarrier-based in situ cell cryopreservation method comprises the following steps:
 (A1) centrifuging a three-dimensional microcarrier suspension of cells and discarding supernatant to obtain a cell-containing carrier;
 (A2) mixing the cell-containing carrier obtained in the step (A1) with a cryopreservation solution and adding to a cryogenic storage tube;
 (A3) cooling down the cryogenic storage tube added with the cell-containing carrier in the step (A2) and then transferring it to liquid nitrogen; enabling in situ cryopreservation of cells on three-dimensional microcarrier.

The method further comprises a method of cell attachment culture on three-dimensional microcarrier, a method for harvesting cells on three-dimensional microcarrier and a method for sampling cells cultured on microcarrier; the method of cell attachment culture on three-dimensional microcarrier is used for inoculating cells on a three-dimensional microcarrier; the method for harvesting cells on three-dimensional microcarrier is used for separating cells from a three-dimensional microcarrier; the method for sampling cells cultured on microcarrier is used for performing calculations of a total number of cells and/or cell density of cells cultured on microcarrier.

The method of cell attachment culture on three-dimensional microcarrier comprises the following steps: (B1) cell inoculation: mixing a cell suspension with a dried three-dimensional microcarrier to obtain a microcarrier mixed with cell suspension; (B2) cell attachment: incubating the microcarrier mixed with cell suspension obtained in the step (B1) so that the cells attach to the three-dimensional microcarrier; (B3) cell culture: after cell attachment in the step (B2), adding a complete culture medium and carrying out culture.

The method for harvesting cells on three-dimensional microcarrier comprises the following steps: (C1) naturally precipitating or centrifuging three-dimensional microcarriers attached with cultured cells, removing supernatant to obtain three-dimensional microcarriers containing cells; (C2) adding lysis solution to the three-dimensional microcarriers containing cells, incubating and lysing the three-dimensional microcarriers therein; (C3) after completely lysing the three-dimensional microcarriers in the step (C2), adding termination solution to terminate the lysis or proceeding directly to step (C4) to terminate the lysis; (C4) centrifuging the system obtained in the step (C3), discarding the supernatant, to harvest cells on the three-dimensional microcarriers.

The method for sampling cells cultured on microcarrier comprises the following steps: (D1) weighing a certain weight of microcarriers for cell culture, placing them in a sampling tube, adding liquid to simulate cell culture process, soaking them at 4 to 60° C. for 0 to 24 hours and then marking a scale corresponding to a volume occupied by the microcarriers on the sampling tube as a standard scale; (D2) sampling cells cultured on the microcarriers as follows: sampling the microcarriers from the cell culture system with the sampling tube to bring volume of the microcarriers to the standard scale.

In the three-dimensional microcarrier-based cell recovery method, the cryopreserved cell microtissues are cells cryopreserved in a three-dimensional microcarrier. There are 0.1 to $25 \times 10^6$ cells per mg of cryopreserved microtissues. In an embodiment of the present invention, there are $0.25 \times 10^6$ cells per mg of microtissues.

The three-dimensional microcarrier-based cell recovery method is a three-dimensional microcarrier-based dynamic cell recovery method or a three-dimensional microcarrier-based static cell recovery method.

The three-dimensional microcarrier-based dynamic cell recovery method comprises the following steps: (E1) taking three-dimensional microcarriers and placing them in a cell culture vessel, adding cell culture medium and immediately proceeding to the next step or processing for more than 1 minutes; the processing method is standing or stirring; (E2) inoculating a cell suspension obtained by thawing cryopreserved cells or cryopreserved cell microtissues at 37° C. into the cell culture vessel containing microcarriers prepared in (E1), then adding cell culture medium and adjusting a ratio of microcarrier to medium to 1 mg:1 to 1000 μL; placing the cell culture vessel on a stirrer and stirring in an incubator; (E3) after completion of (E2), continuing to stir the cells until cell recovery is completed.

The three-dimensional microcarrier-based static cell recovery method comprises the following steps: (F1) preparation of static culture vessel and microcarriers: taking three-dimensional microcarriers and placing them in a cell culture vessel; (F2) thawing of cryopreserved cells and inoculation: taking cryopreserved cells or cryopreserved cell microtissues and thawing them at 37° C. and then inoculating them into the static culture vessel containing microcarriers prepared in (F1) for 20 to 240 minutes; (F3) after completion of (F2), continuing to culture the cells until cell recovery is completed.

In the step (E1), the cell culture medium can be added and then left to stand for 1 to 10 minutes. In an embodiment of the present invention, the standing time is 10 minutes.

In the step (E1), the volume of cell culture medium added is 0 to 50% of that of medium during the stirring and recovery in the step (E2). In an embodiment of the present invention, the volume of cell culture medium added is 1/6 of that of medium during the stirring and recovery in the step (E2).

In the step (E2), the volume of cell suspension after thawing is 1 to 100% of that of the medium during the stirring and recovery in the step (E2). In an embodiment of the present invention, the volume of cell suspension is 1/30 of that of the medium during the stirring and recovery in the step (E2). The cell concentration in the cell suspension is 5 to $500 \times 10^5$ cells/mL. In an embodiment of the present invention, the cell concentration in the cell suspension is $1 \times 10^6$ cells/mL.

In the step (E2), the cells or cell microtissues are inoculated into the cell culture vessel containing microcarriers at a ratio of cell number to microcarrier of $5-100 \times 10^3$ cells/mg of microcarriers. In an embodiment of the present invention, the ratio of cell number to new microcarrier is $10^4$ cells/mg of microcarriers; the ratio of microcarrier to medium is adjusted to 1 mg:300 μL by adding cell culture medium.

In the step (E2), the stirring is constant speed stirring or variable speed alternating stirring or variable speed cyclic stirring.

The stirring is clockwise stirring, anticlockwise stirring or stirring in alternating directions.

The stirring time is between 0.1 and 100 hours (e.g. 96 hours).

The stirring speed is 1 to 200 rpm. The stirring speed is preferably 5 to 80 rpm, more preferably 10 to 60 rpm.

Further, the stirring recovery is carried out as follows (a) or (b) or (c):
 (a) standing for 1 to 4 hours, followed by stirring clockwise at cyclic variable speeds for 1 to 24 hours, followed by stirring clockwise at a constant speed until the 96th hour;
 (b) stirring clockwise at cyclic variable speeds for 1 to 24 hours, followed by stirring clockwise at a constant speed until the 96th hour;
 (c) stirring clockwise at a constant speed for 1 to 96 hours.

In an embodiment of the present invention, the stirring is carried out by standing for 4 hours, then stirring clockwise at cyclic variable speeds in cycles of 40 rpm for 5 minutes and 20 rpm for 20 minutes until the 24th hour and then clockwise at a constant speed (60 rpm) until the 96th hour.

In an embodiment of the present invention, the stirring is carried out by stirring clockwise at cyclic variable speeds for 24 hours in cycles of 40 rpm for 5 minutes and 20 rpm for 20 minutes, and then clockwise at a constant speed (60 rpm) to the 96th hour.

In an embodiment of the present invention, the stirring is carried out at a constant speed (60 rpm) clockwise until the 96th hour.

In the step (E3), the stirring method can be referred to the previous section. In an embodiment of the present invention, the stirring is carried out at a constant speed (60 rpm) clockwise.

In the steps (E1) to (E3), the cell culture vessel is a vessel in which the microcarriers can be stirred up and suspended. The cell culture vessel used in an embodiment of the present invention is a cell culture flask with built-in impeller (Bellco Glass, USA; Catalog No.: 1965-61001).

In the step (F2), the ratio of microcarrier to number of cells is 5 to $100 \times 10^3$ cells/mg microcarriers. In an embodiment of the present invention, the ratio of number of cells to new microcarrier is 10,000 cells/mg microcarriers.

In the step (F2), after inoculation of the cells, the cell culture medium is added to adjust the ratio of medium to microcarrier to 100 to 400 μL:20 mg. In an embodiment of the present invention, the ratio of cell culture medium to microcarrier is 200 μL:20 mg.

In an embodiment of the present invention, the incubation time is 240 minutes.

In the above three-dimensional microcarrier-based cell recovery method, the three-dimensional microcarrier is a three-dimensional porous microcarrier. The three-dimensional porous microcarrier can be specifically a 3D Table-Trix microcarrier (Beijing CytoNiche Biotech Ltd.; Catalog No.: F01-100).

In the three-dimensional microcarrier cell culture-based in situ passaging method, the new microcarrier is a microcarrier that does not contain cells. The seed microcarrier has a cell density of 10,000 to 1,000,000 cells/mg microcarriers (e.g., 100,000 to 500,000 cells/mg microcarriers, or 120,000 to 500,000 cells/mg microcarrier). The ratio of seed microcarrier to new microcarrier is 0.0002 to 200 mg seed microcarriers/mg new microcarriers (e.g., 2 to 15 mg seed microcarriers/100 mg new microcarriers).

Further, the seed microcarrier has a cell density of 120,000 to 500,000 cells/mg microcarriers (particularly suitable for static in situ passaging as described below) or 150,000 to 500,000 cells/mg microcarriers (particularly suitable for dynamic in situ passaging as described below). The ratio of seed microcarrier to new microcarrier is 1 to 3 mg seed microcarriers/20 mg new microcarriers (particularly suitable for static in situ passaging as described below) or 2 to 6.7 mg seed microcarriers/100 mg new microcarriers (particularly suitable for dynamic in situ passaging as described below).

The three-dimensional microcarrier cell culture-based in situ passaging method is a three-dimensional microcarrier cell culture-based dynamic in situ passaging method or a three-dimensional microcarrier cell culture-based static in situ passaging method.

The three-dimensional microcarrier cell culture-based dynamic in situ passaging method comprises the following steps: (G1) preparation of a new microcarrier suspension: placing new microcarriers in a cell culture flask with built-in impeller, adding cell culture medium at a ratio of 1 to 2,000 μL:1 mg microcarriers, and standing or stirring for more than 0 hours to obtain the new microcarrier suspension; (G2) preparation of a seed microcarrier suspension: the seed microcarrier has a cell density of 10,000 to 1 million cells/mg microcarriers, resuspending the seed microcarrier to 0.1 to 50 mg/mL with cell culture medium to obtain the seed microcarrier suspension; (G3) inoculation: mixing the seed microcarrier suspension prepared in (G2) into the cell culture flask with built-in impeller containing the new microcarrier suspension prepared in (G1), the ratio of seed microcarrier to new microcarrier is 0.0002 to 200 mg seed microcarriers/mg new microcarriers, adding cell culture medium to adjust the ratio of microcarrier to medium to 1 mg:1 to 1000 μL, placing the cell culture flask with built-in impeller on a stirrer and placing in an incubator for stirring for 0 to 100 hours; (G4) culture: continue stirring to complete the dynamic in situ passaging.

The three-dimensional microcarrier cell culture-based static in situ passaging method comprises the following steps: (H1) preparation of a seed microcarrier suspension: the seed microcarrier has a cell density of 10,000-1,000,000 cells/mg microcarriers, resuspending the seed microcarrier to 0.1 to 50 mg/mL with cell culture medium to obtain the seed microcarrier suspension; (H2) inoculation: adding dropwise the seed microcarrier suspension prepared in (H1) to a new microcarrier, a ratio of seed microcarrier to new microcarrier is 0.0002 to 200 mg seed microcarriers/mg new microcarriers, mixing well and placing in an incubator for incubation for 0.5 to 24 hours; (H3) culture: adding cell culture medium and continue culturing, i.e. completing the static in situ passaging.

In the step (G1), the ratio of new microcarrier and cell culture medium placed in the cell culture flask with built-in impeller can be 100 mg microcarriers/10 mL cell culture medium; the new microcarrier and the cell culture medium can be left to stand for 0.1 to 24 hours (in a specific embodiment of the present invention, the standing time is specifically 14 hours) after being placed in the cell culture flask with built-in impeller.

In the step (G2), the cell density in the seed microcarrier can be 150,000 to 500,000 cells/mg microcarriers; the content of the seed microcarrier in the seed microcarrier suspension can be 1 to 10 mg/mL (in a specific embodiment of the present invention, the content of the seed microcarrier in the seed microcarrier suspension is specifically 1 mg/mL).

In an embodiment of the present invention, the cell density in the seed microcarrier is specifically 500,000 cells/mg microcarriers; the content of the seed microcarrier in the seed microcarrier suspension is specifically 1 mg/mL.

In an embodiment of the present invention, the cell density in the seed microcarrier is specifically 150,000 cells/mg microcarriers; the content of the seed microcarrier in the seed microcarrier suspension is specifically 1 mg/mL.

In the step (G3), the ratio of seed microcarrier to new microcarrier can be 1 to 10 mg seed microcarriers/100 mg new microcarriers (e.g. 2 to 6.7 mg seed microcarriers/100 mg new microcarriers); the ratio of microcarrier to medium can be adjusted to 1 to 10 mg:1 mL (e.g. 106.7 to 204 mg:60 mL) by adding the cell culture medium; the stirring speed can be 1 rpm to 200 rpm, the stirring can be by constant speed stirring or variable speed alternating or variable speed cyclic stirring, the stirring direction can be clockwise stirring, counter clockwise stirring or alternating direction stirring, so as to transfer the cells on the seed microcarrier to the new microcarrier.

In an embodiment of the present invention, the ratio of seed microcarrier to new microcarrier is specifically 2 mg seed microcarriers/100 mg new microcarriers; the ratio of microcarrier to medium is specifically adjusted to 204 mg:60 mL by adding the cell culture medium; the stirring is specifically variable speed cyclic clockwise stirring with specific parameters of 60 rpm for 5 mins, 20 rpm for 20 mins in total cycle of 24 hours.

In an embodiment of the present invention, the ratio of seed microcarrier to new microcarrier is specifically 6.7 mg seed microcarriers/100 mg new microcarriers; the ratio of microcarrier to medium is specifically adjusted to 106.7 mg:60 mL by adding the cell culture medium; the stirring is specifically variable speed cyclic clockwise stirring with specific parameters of 60 rpm for 5 mins, 20 rpm for 20 mins in total cycle of 24 hours.

In the step (H1), the cell density in the seed microcarrier can be 120,000 to 500,000 cells/mg microcarriers; the content of the seed microcarrier in the seed microcarrier suspension can be 5 to 15 mg/mL.

In an embodiment of the present invention, the cell density in the seed microcarrier is specifically 500,000 cells/mg microcarriers; the content of the seed microcarrier in the seed microcarrier suspension is specifically 5 mg/mL.

In an embodiment of the present invention, the cell density in the seed microcarrier is specifically 120,000 cells/mg microcarriers; the content of the seed microcarrier in the seed microcarrier suspension is specifically 15 mg/mL.

Further, in the step (H2), the ratio of seed microcarrier to new microcarrier can be 1 to 3 mg seed microcarriers/20 mg new microcarriers; the incubation time can be 0 to 24 hours.

In an embodiment of the present invention, the ratio of seed microcarrier to new microcarrier is specifically 1 mg seed microcarriers/20 mg new microcarriers; the incubation time is specifically 2 hours.

In an embodiment of the present invention, the ratio of seed microcarrier to new microcarrier is specifically 3 mg seed microcarriers/20 mg new microcarriers; the incubation time is specifically 2 hours.

wherein the full incubation time of the method may depend on the cells, the ratio of seed and new carrier provided, the desired number of cells to be finally obtained, and the like.

In the three-dimensional microcarrier cell culture-based in situ passaging method, the microcarrier is 3D FloTrix® microcarrier (Beijing CytoNiche Biotech Ltd.; Catalog No.: CNF-F01T-50), a three-dimensional porous microcarrier. The cell culture flask with built-in impeller is a product of Bellco Glass, USA, with Catalog No.: 1965-61001. The stirrer is a low speed stirrer (3D FloTrix® miniSpin low speed stirrer, Beijing CytoNiche Biotech Ltd.; Catalog No.: 3D FTmS-2-2).

In the three-dimensional microcarrier-based in situ cell cryopreservation method, in the step (A1) the centrifugation is at a speed of 50 to 1610×g, specifically 400×g, for a time of 1 to 10 minutes, specifically 2 minutes. In the step (A2), the ratio of volume of cryopreservation solution to mass of cell-containing carrier is 1 mL: 0.1 to 50 mg, specifically 1 mL: 10 mg or 1 mL: 0.1 to 20 mg.

In the three-dimensional microcarrier-based in situ cell cryopreservation method, the cryopreservation solution comprises 10% DMSO, 10 to 90% FBS and 0 to 80% basal medium, 10% DMSO and 0 to 80% basal medium, 10 to 90% FBS and 0 to 80% basal medium or other commercially available cell cryopreservation solutions, such as CF0101 Cellregen serum-free Cell Cryopreservation Solution.

In the three-dimensional microcarrier-based in situ cell cryopreservation method, the cryogenic storage tube is placed in a refrigerator and cooled to −20 to −196° C., specifically −20 to −80° C.; the cooling is programmed or non-programmed; the programmed cooling has a cooling rate of −1 to −15° C./min; the cooling time can be 1 to 24 hours, specifically 24 hours, 10 to 24 hours or 15 to 24 hours.

In the three-dimensional microcarrier-based in situ cell cryopreservation method, the cooling is performed by placing the cryogenic storage tube in the step (A2) into a cell cooling box and placing it in a refrigerator within 1 to 10 minutes for cooling.

In the three-dimensional microcarrier-based in situ cell cryopreservation method, the 37° C. pre-warmed PBS or basal medium added to the cryogenic storage tube is diluted in a ratio that can be 1:5 to 30.

In the three-dimensional microcarrier-based in situ cell cryopreservation method, the step (A3) is followed by a cell recovery step: the cells are recovered by placing the cryogenic storage tube after the treatment in the step (A3) in a water bath and removing the water bath when the ice in the cryogenic storage tube melts; then diluting the cells by adding 37° C. pre-warmed PBS or basal medium and then centrifuging.

In the three-dimensional microcarrier-based in situ cell cryopreservation method, the temperature of water bath can be 35 to 40° C.; the time of water bath can be 1 to 5 min.

In the three-dimensional microcarrier-based in situ cell cryopreservation method, the speed of centrifugation can be 50 to 1610×g, specifically 400×g, for a time of 1 to 10 minutes, specifically 2 minutes, when the cells are recovered after the step (A3).

In the method of cell attachment culture on three-dimensional microcarrier, the cell suspension has a density of $1\times10^4$ to $1\times10^8$ cells/mL; the cell suspension is obtained by resuspending the cells in culture medium or liquid biological matrix material, wherein the material can be specifically selected from the group consisting of collagen, gelatin, gelatin derivatives, proteoglycans, glycoproteins, alginate, alginate derivatives, agar, matrix gum, hyaluronic acid, fibronectin or laminin. A ratio of volume of the cell suspension to mass of the three-dimensional microcarrier is 1 to 1000 μL:1 mg; specifically, 10 μL:1 mg, 1 to 10 μL:1 mg, 10 to 15 μL:1 mg, 5 to 15 μL:1 mg or 250 to 350 μL:1 mg.

In the method of cell attachment culture on three-dimensional microcarrier, in the step (B1), the cell suspension is mixed with the three-dimensional microcarrier as follows: the cell suspension is added dropwise to the three-dimensional microcarrier. In the step (B1), a dried three-dimensional microcarrier is used and the cell suspension is mixed directly with it, eliminating the need for the three-dimensional microcarrier to be swollen in advance and therefore simplifying the inoculation of cells into the microcarrier.

In the method of cell attachment culture on three-dimensional microcarrier, the incubation conditions can be as follows: a temperature of 35 to 40° C., specifically 37° C., 37 to 40° C. or 35 to 37° C.; a period of 0.5 to 24 hours, specifically 2 hours or 24 hours; a percentage concentration of carbon dioxide by volume of 5 to 30%, specifically 5%, 5 to 10% or 5 to 20%. The attachment method comprises gravity attachment method, swelling attachment method, stirrer rotary attachment method, centrifugal method, surface acoustic wave method or magnetic attachment method.

In the method of cell attachment culture on three-dimensional microcarrier, the conditions of culture are as follows: the temperature can be 35 to 40° C., specifically 37° C., 37 to 40° C. or 35 to 37° C., and the percentage concentration of carbon dioxide by volume can be 5 to 30%, specifically 5%, 5 to 10% or 5 to 20%.

In the method of cell attachment culture on three-dimensional microcarrier, the step (B1) is preceded by a step of gas sterilizing, radiation sterilizing or UV sterilizing the three-dimensional microcarrier.

In the method of cell attachment culture on three-dimensional microcarrier, the three-dimensional microcarrier is a porous microcarrier, specifically 3D FloTrix® microcarrier, commercially available from Beijing CytoNiche Biotech Ltd., with Catalog No.: CNF-F01T-50; Cytopore 1 and Cytopore 2, commercially available from GE, Catalog Nos.: 17-0911, and 17-1271; CultiSpher (M9418), commercially available from Sigma.

In the method for harvesting cells on three-dimensional microcarrier, the lysis solution comprises an active ingredient for lysing the microcarrier with the elimination of cell attachment. The active ingredient is selected from an aqueous solution of at least one of collagenase, pepsin, hyaluronidase, dispase, neutral protease, proteinase K, matrix metalloproteinase, sodium citrate, trypsin, deoxyribonuclease, trypsin substitute, protein hydrolase, ethylene diamine tetraacetic acid, lysozyme and glutathione. In an embodiment, the lysis solution formulation comprises: 0.1%

(mass percentage) collagenase, 0.1% (mass percentage) ethylene diamine tetraacetic acid, and 0.05% (mass percentage) trypsin.

In the method for harvesting cells on three-dimensional microcarrier, the termination solution, depending on the selected composition of the lysis solution, is selected from at least one of whole medium, PBS containing 10% serum albumin or serum, trypsin inhibitor, protease inhibitor, PBS and ionic chelating agent. The ionic chelating agent can specifically be ethylene diamine tetraacetic acid.

In the method for harvesting cells on three-dimensional microcarrier, in the step (C1), the centrifugation can be at a speed of 50 to 1610×g, specifically 200×g, for a time of 1 to 10 minutes, specifically 2 minutes. The step for removing the supernatant is as follows: centrifuging and pipetting the supernatant; then adding an appropriate amount of PBS, shaking gently by hand for 20 to 30 seconds, pipetting the supernatant and repeating the PBS wash once.

In the method for harvesting cells on three-dimensional microcarrier, a ratio of the mass of three-dimensional microcarrier for adsorbing and culturing cells to the volume of lysis solution can be 1 mg:0.01 to 5 mL, specifically 20 mg:3 mL, 1 mg:0.15 to 0.5 mL or 1 mg:0.1 to 2 mL; the incubation can be at a temperature of 4° C. to 40° C., specifically 37° C., for a period of 10 seconds to 24 hours, specifically 30 minutes. In a specific embodiment, during the incubation period described, blowing is gently performed several times using a 1 mL pipette at 10 minutes intervals.

In the method for harvesting cells on three-dimensional microcarrier, the ratio of the mass of three-dimensional microcarrier for adsorbing and culturing cells to the volume of termination solution can be 1 mg:0.01 to 50 mL, specifically 20 mg:3 mL or 1 mg:0.1 to 25 mL.

In the method for harvesting cells on three-dimensional microcarrier, in the step (C4), the centrifugation is at a speed of 50 to 1610×g, specifically 400×g, for a time of 1 to 10 minutes, specifically 2 minutes or 2 to 8 minutes.

The method for sampling cells cultured on microcarrier for calculation of total number of cells and/or cell density of the cells cultured on microcarrier comprises the following steps: (D1) weighing a certain weight of microcarriers for cell culture, placing them in a sampling tube, adding liquid to simulate cell culture process, soaking them at 4 to 60° C. for 0 to 24 hours and then marking a scale corresponding to a volume occupied by the microcarriers on the sampling tube as a standard scale; (D2) sampling cells cultured on the microcarrier as follows: sampling the microcarriers from the cell culture system with the sampling tube to bring the volume of the microcarriers to the standard scale; (D3) counting the cells in the microcarriers collected in (D2); (D4) calculating the total number of cells in the entire cell culture system based on the weight of microcarriers weighed in (D1), the number of cells counted in (D3) and the total weight of microcarriers in the entire cell culture system; and thus calculating the cell density.

In the step (D1), the process of adding liquid to the sampling tube containing the microcarrier and soaking for 0 to 24 hours at 4 to 60° C. is the process of full immersion and swelling of the microcarrier. Wherein the liquid added can be of the same or similar viscosity, hydrophilicity, pH, ionic concentration as the medium of the present invention used for cell culture on the microcarrier (e.g. the medium of the present invention used for cell culture or PBS). The temperature and time required to soak and swell the microcarrier varies depending on the microcarrier. This can be done according to the instruction for microcarrier from different manufacturers. For example, using microcarrier Cytodex 1 available from GE, the dried microcarrier is swollen by immersion in PBS at room temperature for at least 3 hours at a ratio of 30-50 mL/g. For example, the 3D FloTrix® microcarrier (CNF-F01T-50) available from Beijing CytoNiche Biotech Ltd. is soaked and swollen in PBS at room temperature for 0.5 to 24 hours; specifically 6 hours, at a ratio of 10 to 1000 µL:1 mg; specifically 10 µL:1 mg, 10 to 15 µL:1 mg, 5 to 15 µL:1 mg or 250 to 350 µL:1 mg.

In the step (D1), after immersing the microcarriers in the liquid, a further step of natural precipitation or centrifugal precipitation (e.g. centrifugation at 1,500 rpm for 2 min) is also comprised, with the aim of precipitating the microcarriers as quickly as possible.

In the step (D2), the sampling of microcarriers from the cell culture system using the sampling tube can be carried out according to a method comprising the following steps: pipetting the suspension from the cell culture system, adding it to the sampling tube, and allowing the microcarriers to precipitate either naturally or by centrifugation (centrifugation can be at a speed of 50 to 1610×g, specifically 200×g, for a period of 1 to 10 minutes, specifically 2 minutes, in order to speed up the precipitation) and observing whether a volume of the microcarriers reaches the standard scale calibrated in the step (D1); if not reached, continuing to pipette the suspension until the standard scale is reached, and if exceeded, removing excess of the microcarriers from the sampling tube.

In the step (D3), the counting of cells in the microcarriers collected in (D2) can be carried out according to a method comprising the following steps: centrifuging the sampling tube in (D2) (e.g. 200×g for 2 minutes), discarding the supernatant, adding cell digestion solution to the precipitate to digest the cells off the microcarriers and then counting.

In the step (D4), the total number of cells in the whole cell culture system is equal to the number of cells counted in (D3) multiplied by the total weight of microcarriers related to the weight of microcarriers weighed in (D1) above.

In the step (D4), the total number is divided by the total weight or total number of microcarriers or the total volume of the culture system to obtain cell density in different units, e.g. cells/mg microcarriers, cells/microcarriers, cells/mL culture system.

In the method for sampling cells cultured on microcarrier, the microcarrier is 3D FloTrix® microcarrier (Catalog No.: CNF-F01T-50) available from Beijing CytoNiche Biotech Ltd. The sampling tube is specifically a 1.5 ml microcentrifuge tube.

In an embodiment, the weight of microcarriers weighed in the step (D1) is 5 mg; the sampling tube is a 1.5 ml microcentrifuge tube; the standard scale is a 0.1 mL scale; the weight of microcarriers in the cell culture system is 200 mg, the initial number of cells in culture is 2 million, the medium in the culture system has a volume of 60 mL; and the sampling is performed after 72 hours of cell culture.

Any of the above methods further comprises a three-dimensional microcarrier-based method for large-scale expansion of cells, which comprises the following steps: achieving large-scale expansion of cells on three-dimensional microcarriers in a stirred bioreactor.

The stirred bioreactor may include, but is not limited to, semi-automatic, fully automatic, or integrated bioreactors. The stirred bioreactor can be specifically either a 3D FloTrix® miniSpin small-scale bioreactor or a 3D FloTrix® vivaSpin bioreactor. One bioreactor alone or two bioreactors in combination can be used.

The conditions under which cells are cultured in the bioreactor can be controlled according to the growth of the cells. For example, the incubation pH can be of 6.5 to 7.5, preferably 7.0 to 7.5, more preferably 7.2; the active pumping of $CO_2$ can be of about 3 to 10%, preferably about 5 to 8%, more preferably about 5; the temperature can be of 30° C. to 40° C., preferably 37° C.; the stirring speed can be of 10 to 150 rpm, preferably 40 to 80 rpm; the frequency of gas delivery can be of 1 to 40 ccm; more preferably about 5 to 20 ccm.

In an example of the present invention, cells were inoculated into three-dimensional microcarriers and then placed in a 3D FloTrix® miniSpin small-scale bioreactor for culture for 6 days at a constant clockwise speed of 60 rpm before being transferred to a 3D FloTrix® vivaSpin bioreactor. The process parameters set for the 3D FloTrix® vivaSpin bioreactor were controlled as follows: active pumping of 12 ccm of 5% $CO_2$ throughout the process, and a temperature of 37° C. 800 mL of complete medium was actively pumped in at a rate of 10 mL/min at T=0 hour, 500 mL of liquid was actively pumped out at a rate of 10 mL/min followed by 500 mL of fresh medium pumped in at a rate of 10 mL/min at T=96 hour, 500 mL of liquid was actively pumped out at a rate of 10 mL/min followed by 50 tablets of 3D Table Trix™ microcarriers resuspended in 500 mL of fresh medium actively pumped into the reactor at 10 mL/min at T=144 hours. The stirring rates for T=0 to 12 hour and T=144 to 156 hour were variable speeds in cycles of 40 rpm for 5 minutes, 20 rpm for 20 minutes and a constant speed of 60 rpm for the rest of the time.

In another example of the present invention, cells were inoculated into three-dimensional microcarriers and then inoculated directly into a 3D FloTrix® vivaSpin bioreactor. The process parameters set for the 3D FloTrix® vivaSpin bioreactor were controlled as follows: active pumping of 10 ccm of 5% $CO_2$ throughout the process, and a temperature of 37° C. 460 mL of complete medium was actively pumped in at a rate of 10 mL/min at T=0 hour, followed by 500 mL of liquid actively pumped out at a rate of 10 mL/min at T=48 hour. Every 24 hours thereafter, 500 mL of liquid was actively pumped out at a rate of 10 mL/min followed by 500 mL of fresh medium actively pumped into the reactor at a rate of 10 mL/min until 120 hours. After actively pumping out 500 mL of liquid n at 10 mL/min at T=120 hour, 40 tablets of 3D TableTrix™ microcarriers resuspended in 500 mL of fresh medium were actively pumped into the reactor at a rate of 10 mL/min. The stirring rate for T=0 to 120 hour was a constant speed of 60 rpm; for T=120 to 136 hour, the stirring rates were variable speeds in cycles of 60 rpm for 5 minutes and 20 rpm for 20 minutes; for T=136 to 240 hour, the stirring rate was a constant speed of 60 rpm (after 240 hours, the stirring mode was a constant speed of 60 rpm).

Any of the above three-dimensional microcarriers may specifically refer to microcarrier beads with a porous structure, wherein the cells to be cultured are cultured on the three-dimensional microcarriers within a cell culture vessel (e.g. cell culture flask, well plate or bioreactor). In microcarrier culture, cells can attach to the surface of the three-dimensional microcarriers and inside the internally connected pores, while the microcarriers can be suspended in the culture medium in the culture vessel by gentle stirring. Exemplary three-dimensional microcarriers include, but are not limited to, 3D Table Trix™ microcarrier, 3D FloTrix® microcarrier, and the like.

Any of the above cells is adherent cell, which can specifically be stem cell. The stem cell includes, but is not limited to, mesenchymal stem cell (MSC), embryonic stem cell (ESC), adipocyte stem cell (ADSC), neural stem cell (NSC), induced pluripotent stem cell (iPSC) of various tissue sources and cell derived from stem cell, etc. The stem cell can in particular be mesenchymal stem cell. The MSC can specifically be adipose-derived MSC or umbilical cord MSC.

DETAILED DESCRIPTION OF THE INVENTION

The following embodiments/examples facilitate a better understanding of the present invention, but do not limit the present invention. The experimental methods in the following embodiments/examples were all routine methods unless otherwise specified. The test materials used in the following embodiments, unless otherwise specified, were all purchased from routine biochemical reagent stores. The quantitative tests in the following embodiments/examples were set up in three replicate experiments and the average value was taken as the result.

Example 1: Method of Three-Dimensional Microcarrier Cell Attachment Culture

The microcarrier used in the example was 3D FloTrix® microcarrier, purchased from Beijing CytoNiche Biotech Ltd., with Catalog No. of CNF-F01T-50.

Figure 1:
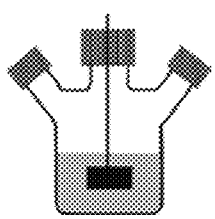
FIG. 1 shows a cell culture flask with built-in impeller used in Example 1 of the present invention.
Figure 2:
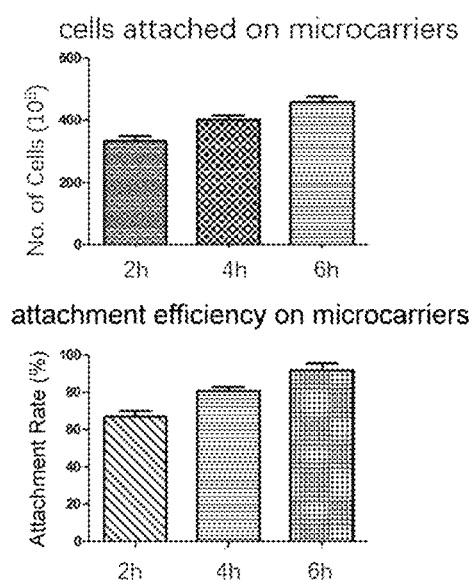
FIG. 2 shows the numbers of cells gradually adsorbed onto the microcarriers by the rotary attachment method of cells and microcarriers and the attachment efficiency in Example 1 of the present invention.

I. A Method of Three-Dimensional Microcarrier Cell Attachment Using Stirrer Rotary Attachment;
1. Microcarrier preparation: 200 mg of microcarrier powder was weighed for ultraviolet sterilization and then poured into a sterile cell culture flask with built-in impeller (as shown in FIG. 1); three groups were prepared;
2. Cell preparation: The adipose-derived MSC suspension was prepared in advance, and $5×10^6$ cells were resuspended in 60 mL complete medium for later use; three groups were prepared;
3. Cell inoculation: The cell suspensions above were mixed into the cell culture flask with built-in impeller, and mixed well with 200 mg of microcarriers;
4. Cell attachment: The cell culture flask with built-in impeller was placed on a low-speed stirrer and placed in a 37° C., 5% $CO_2$ incubator for stirring at 80 rpm to allow the cells to attach to the microcarriers by rotation;
5. In-situ counting to obtain attachment rate:
   a. Microcarrier collection: Three groups of microcarriers were mixed with the cell suspension after 2, 4 and 6 hours of stirring, respectively, and then collected through a 70 μm cell sieve and washed once with PBS to wash off any cells not attached to the microcarriers. The microcarrier suspension containing the cells was then centrifuged at 1500 rpm for 2 minutes and the supernatant was discarded.
   b. Cell counting: 200 mg of microcarriers were added to 50 mL of 0.1% crystal violet solution (0.1 g of crystalline violet, 2.1 g of citric acid, 20 μL of Tween-80, 100 ml of deionized water) at 37° C. for 2 to 5 hours, the cells were counted with a cell counting plate, and the attachment rate was obtained after conversion according to the initial inoculation number.
   c. Result analysis: FIG. 2 shows that with increasing stirring time, the cells were able to gradually attach to the microcarriers by rotary attachment, with attachment efficiency reaching 67% at 2 hours of stirring, 81% at 4 hours and 92% at 6 hours.

II. A Method of Three-Dimensional Microcarrier Cell Attachment Using Small Volume High Density Swelling Attachment 1. Microcarrier preparation: 20 mg of microcarrier powder was weighed for ultraviolet sterilization for later use;
2. Cell preparation: The adipose-derived MSC suspension were prepared in advance, with a density of $2.5 \times 10^6$ cells/mL, and 200 µL was prepared for every 20 mg of three-dimensional microcarriers;
3. Cell inoculation: 200 µL of cell suspension was pipetted and added dropwise into 20 mg of microcarriers, so that the cell suspension was well mixed with the microcarriers;
4. Cell attachment: The microcarriers mixed well with cell suspension were placed into a 37° C., 5% $CO_2$ incubator to incubate for 2 hours, allowing the cells to attach to the microcarriers;
5. Cell culture: After the cells have attached, 3 mL of complete medium was added and the cells are incubated at 37° C. in a 5% $CO_2$ incubator for 24 hours and then observed.
6. Control experiment: Steps 3 to 5 adopted the small volume high density attachment method, which is the method of the present invention; in addition, a control experimental group for the common attachment method (large volume low density) was prepared, i.e., 200 µL of cell suspension were mixed into 3 mL of complete medium, 20 mg of microcarriers were added directly, and the cells were observed 24 hours thereafter.
7. Cell observation:
1) Kit: Live & Dead Viability/Cytotoxicity Assay Kit for Animal Cell, Catalog No.: KGAF001;
2) 50 to 100 µL of a three-dimensional microcarrier suspension containing cells was added to a 96-well plate.
3) The supernatant was removed as much as possible, PBS was added and washed once, PBS was removed as much as possible after 2 minutes, each well was stained by adding 100 µL of the staining solution configured according to the instructions of the kit. After staining for 20 to 30 minutes at room temperature and protected from light, observation was carried out under a fluorescent microscope; the results are shown in FIG. 3.

Figure 3:
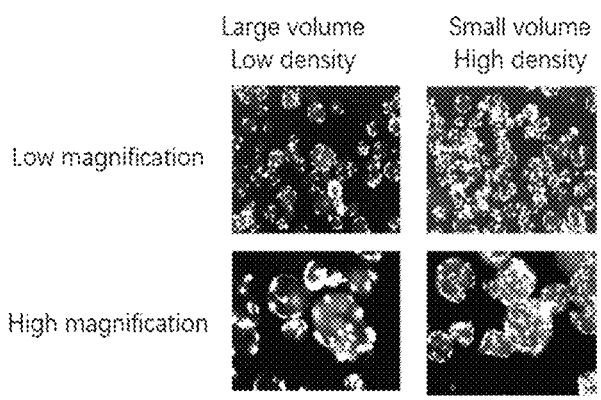
FIG. 3 shows a graph of the results of fluorescent staining after cell attachment by the method in Example 2 of the present invention.

As can be seen from FIG. 3, live cells were stained with the staining solution and could be observed to glow by fluorescence and the cells that glow were the live cells. The figure shows that by the large volume low density attachment method, a few cells were attached on the microcarriers and mainly on the surface of the microcarriers, whereas by the small volume high density attachment method, a large number of cells can be attached on the microcarriers and the cells were present not only on the surface of the microcarriers but also in the pores of the porous microcarriers, thus showing that the small volume high density attachment method of the present invention can be more effective in attaching cells onto the microcarrier and better utilizing the large area of the porous microcarriers.

Example 2 Method for Harvesting Cells on Three-Dimensional Microcarrier

The microcarrier used in the example was 3D FloTrix® microcarrier, purchased from Beijing CytoNiche Biotech Ltd., with Catalog No. of CNF-F01T-50.

1. Lysis solution formulation: 0.1% (mass percentage) collagenase (Sigma-Aldrich (Shanghai) Trading Co., Ltd., C0130), 0.1% (mass percentage) EDTA (Beijing Solarbio Science & Technology Co., Ltd., E1170), 0.05% (mass percentage) trypsin (M & C Gene Technology (Beijing) Ltd., CC017); terminating solution: complete medium;
2. 20 mg of three-dimensional microcarriers with adipose-derived MSCs from the culture dish were transferred to a centrifuge tube, centrifuged at 400×g for 2 minutes, the supernatant was pipetted, an appropriate amount of PBS was added, shaken gently by hand for 20 to 30 seconds, the supernatant was pipetted as much as possible and the PBS wash was repeated once.
3. 3 mL of lysis solution was added, and the cells were incubated in a cell incubator at 37° C. for 30 minutes, gently blown several times with a 1 ml pipette every 10 minutes during the period.
4. after 30 minutes, the microcarriers were completely lysed, and 3 mL of whole medium was added to terminate the lysis process.
5. Centrifuge was performed at 200×g for 5 minutes, the supernatant was discarded, and cells were resuspended as required for subsequent applications.
6. Cell detection method:
(1) In Situ Calcein-AM/PI Staining Method of Living Cells:
1) Kit: Live & Dead Viability/Cytotoxicity Assay Kit for Animal Cell, Catalog No.: KGAF001;
2) 20 mg of 3D microcarrier suspension containing cells was added into a centrifuge tube; centrifuged at 400×g for 2 minutes;
3) The supernatant was removed as much as possible, PBS was added and washed once, PBS was removed as much as possible after 2 minutes, 100 µL of the staining solution configured according to the instructions of the kit was added for staining. After staining for 20 to 30 minutes at room temperature and protected from light, the tube centrifuged at 400×g for 2 minutes;
4) The supernatant was discarded, 3 mL of lysis solution was added and the microcarrier lysis was observed under light microscopy and the live cells were observed under fluorescence microscopy at 0 minute, 10 minutes and 30 minutes; the results are shown in FIG. 4.

Figure 4:
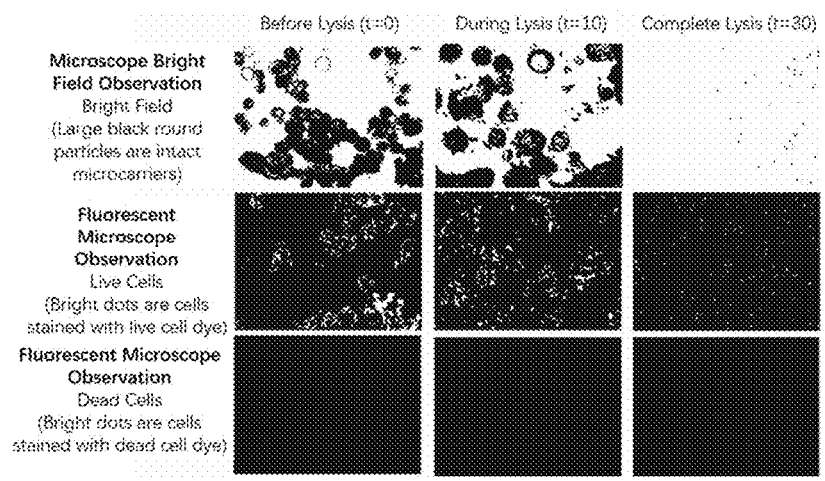
FIG. 4 shows a diagram of the microcarrier lysis observed under the bright field of the microscope and the live cells observed under the fluorescence microscope in Example 2 of the present invention.

As can be seen in FIG. 4, the microcarriers were observed in the bright field of the light microscope to gradually lyse and disappear over time, leaving only the cells behind. Observation of the stained cells by fluorescence microscopy light showed that as the lysis solution lysed the microcarriers, the cells were detached from the microcarriers into single cells, while the number of dead cells did not increase and the cells remained active. This indicated that lysis against the microcarriers was able to harvest the cells from the microcarriers without affecting their activities.

(2) Analytical Method for Determining Apoptosis Rate by Flow Cytometry:
1) Cell collection: 20 mg of three-dimensional microcarrier suspension containing cells was centrifuged at 400×g for 2 minutes, and the supernatant was discarded. 3 mL of 0.1% Collagenase Type IV solution (1 g of Collagenase Type IV (Gibco, 17104019) dissolved in 1 L of PBS) was added, and the solution was incubated in a cell incubator at 37° C. for 30 minutes, and centrifuged at 400×g for 5 minutes, and the supernatant was discarded. For the harvesting of two-dimensional (2D) cells, the conventional trypsin digestion method was used, that is, the medium in the cell culture flask was discarded, the appropriate amount of PBS was added and washed twice, the appropriate amount of 0.25% trypsin solution was added and the cells were incubated at 37° C. for 2 minutes or until they detached from the flask. After termination by adding an equal amount of complete medium, the suspension was removed into a centrifuge tube and centrifuged at 400×g for 5 minutes, the supernatant was discarded.

2) Cell washing: The cells were resuspended once by precooled PBS at 4° C. and centrifuged at 400×g for 5 minutes, then the cells were washed.

3) Cell staining: Cells were stained using Annexin V-FITC/PI Apoptosis Detection Kit (HaiGene Biotech Co., Ltd, S0185), that is, 300 μL of Binding Buffer was added, followed by 5 μL of Annexin V-FITC, mixed and incubated for 15 minutes at room temperature, protected from light; 5 μL of PI was then added for staining for 5 minutes; supplemented with 200 μL of Binding Buffer.

4) Cell flow cytometry: Flow cytometry of the stained cells was performed using BD FACSAria II Flow Cytometer and a report of the cell classification analysis was generated by the instrument.

5) Interpretation of the cell flow cytometry report:

A) Annexin-V negative-PI-negative represents normal cells, i.e. the lower left group in the four-frame cell classification diagram, whose proportion of cells is the proportion of live cells.

B) Annexin-V positive-PI-negative represents cells in the early stages of apoptosis, i.e. the lower right group in the four-frame cell classification diagram, whose proportion of cells is the proportion of cells in the early stages of apoptosis.

C) Annexin-V positive-PI positive represents cells in the later stage of apoptosis or necrotic cells, i.e. the upper right group in the four-frame cell classification diagram, whose proportion of cells is the proportion of cells in the later stage of apoptosis.

Figure 5:
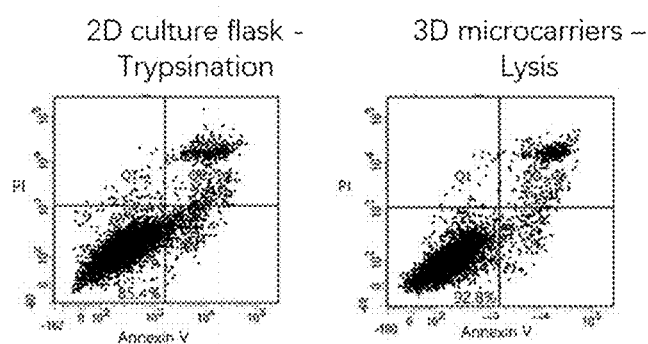
FIG. 5 shows the comparison results of the activity of cells on three-dimensional microcarrier (3D FloTrix® microcarrier) harvested from lysis solution in Example 2 of the present invention compared to the activity of cells in culture flask obtained by conventional trypsination.

As can be seen from the results in FIG. 5, the activity of cells harvested on three-dimensional microcarriers (3D FloTrix® microcarriers) by lysis solution was similar to, or even slightly higher than, the activity of cells obtained in culture flask by conventional trypsin digestion, indicating that the present invention is effective in harvesting cells with high activity by targeting the microcarriers with lysis solution and thereby harvesting cells on the microcarriers.

Example 3 a Method for Sampling and Counting Cells Cultured on Microcarrier

The microcarrier used in the example was 3D FloTrix® microcarrier, purchased from Beijing CytoNiche Biotech Ltd., with Catalog No. of CNF-F01T-50.

The cells involved in the example were mesenchymal stem cells.

Design concept: In the present invention, a standard scale is calibrated by measuring the volume of a certain weight of microcarriers. When using microcarriers for cell culture, the volume of microcarriers to be sampled (not related to the volume of the culture medium) is required to reach the standard scale and then the cells are counted and converted to the whole culture system to obtain the total number of cells, this method is called microcarrier quantitative sampling method.

Figure 6:
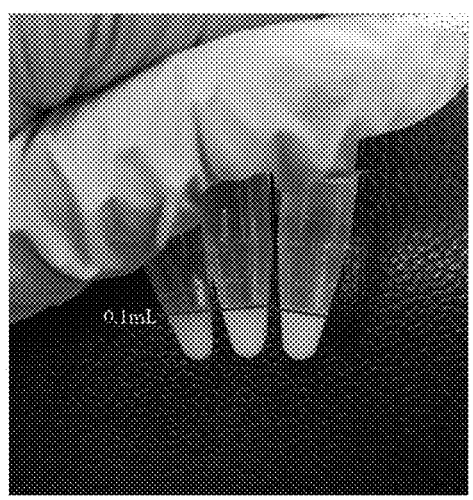
FIG. 6 shows that 5 mg microcarriers reaches a scale that exactly matches the 0.1 mL scale on a 1.5 ml microcentrifuge tube in Example 3 of the present invention.

Examples of Specific Protocols 1. 5 mg of microcarriers were added into 1.5 mL sampling tube (microcentrifuge tube), and dissolved in 1 mL of PBS, fully soaked and swollen, then centrifuged at 1500 rpm for 2 minutes to calibrate the volume occupied by the microcarriers in the sampling tube. In the example, it was found that 5 mg of microcarrier was precipitated to a scale that exactly matched the 0.1 mL scale on the 1.5 mL sampling tube (FIG. 6).

2. After resuspension of 2 million cells in 60 mL of medium, 200 mg of microcarriers were added and incubated at 37° C. in a 5% $CO_2$ incubator.

Figure 7:
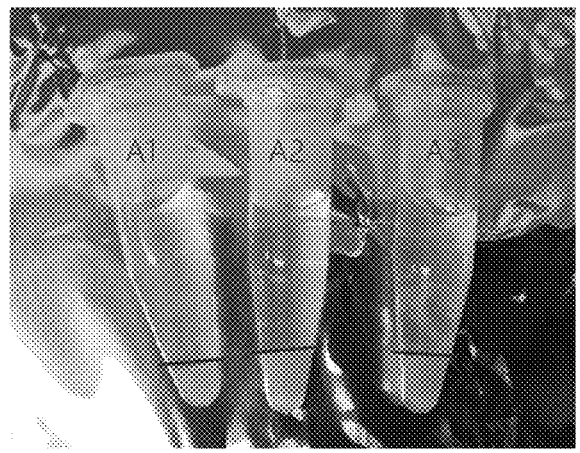
FIG. 7 shows the state of 1 mL of suspension pipetted by the suspension quantitative sampling method after natural precipitation in Example 3 of the present invention. A1 to A3 indicates three replicates.

3. After 72 hours, two sampling methods were used, as follows:

(a) The microcarriers were suspended as evenly as possible in 60 mL of medium by shaking the culture vessel and 1 mL of suspension was pipetted as soon as possible and added to 1.5 mL sampling tube. A total of 3 tubes were pipetted (see FIG. 7). This was the suspension quantitative sampling method.

Figure 8:
FIG. 8 shows the state of 1 mL of suspension pipetted by the microcarrier quantitative sampling method after natural precipitation in Example 3 of the present invention. B1 to B3 indicates three replicates.

(b) The microcarriers were suspended in the medium by shaking the culture vessel, the suspension was pipetted into a 1.5 mL sampling tube. After waiting a few minutes for the microcarriers to settle, it was observed whether the volume of microcarriers reached the standard scale calibrated in step 1, in the example a standard scale of 0.1 mL was used (corresponding to 5 mg of microcarriers, FIG. 6). If not, it was continued to pipette the suspension until the scale was reached, and if exceeded, the excess microcarriers were removed from the sampling tube. A total of 3 tubes were pipetted (see FIG. 8). This was the microcarrier quantitative sampling method.

4. The above sampling tubes were centrifuged at 1500 rpm for 2 minutes, and the supernatant was discarded. The cells were digested from the microcarriers by adding cell digestion solution and then counted and the total number of cells in the culture system was inferred according to the corresponding formula depending on the sampling method.

(a) Suspension quantitative sampling method: Cell number of 1 mL of suspension sample×Total suspension volume of culture system (i.e., 60 mL)=Total cell number.

Results are as shown in Table 1.

TABLE 1

Statistical results of the total number of cells from three replicates of the suspension quantitative sampling method

| Replicate | Number of sampled cells (100,000) | Volume of sampled suspension (mL) | Total suspension volume (mL) | Total cell number (100,000) |
|---|---|---|---|---|
| A1 | 0.25 | 1 | 60 | 21 |
| A2 | 2.2 | 1 | 60 | 132 |
| A3 | 1.58 | 1 | 60 | 94.8 |
| | Mean | | | 80.60 |
| | Standard deviation | | | 59.78 |

(b) Microcarrier quantitative sampling method: Cell number of 5 mg of microcarrier (i.e., 0.1 mL microcarrier volume) sample×Total microcarrier weight of culture system (i.e., 200 mg)=Total cell number.

Results are as shown in Table 2.

TABLE 2

Statistical results of the total number of cells from three replicates of the microcarrier quantitative sampling method

| Replicate | Number of sampled cells (100,000) | Weight of sampled microcarriers (mg) | Total microcarrier weight (mg) | Total cell number (100,000) |
|---|---|---|---|---|
| B1 | 1.55 | 5 | 200 | 62 |
| B2 | 1.65 | 5 | 200 | 66 |
| B3 | 1.58 | 5 | 200 | 63.2 |
| | | | Mean | 63.73 |
| | | | Standard deviation | 2.05 |

5. All microcarrier suspensions from the 200 mg of microcarriers, 60 mL of medium culture system were removed, centrifuged at 1500 rpm for 2 minutes, the supernatant discarded, the cells were digested off the microcarrier by adding cell digestion solution and the actual total number was counted and compared with the data from the sampling counts in step 4.

Figure 9:
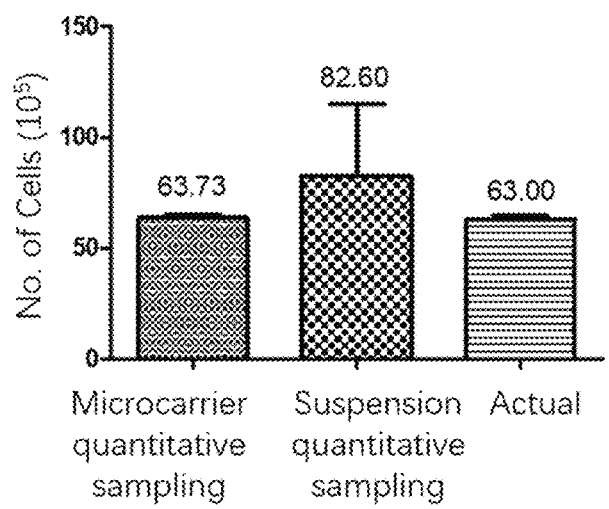
FIG. 9 shows the comparison results of the total numbers of cells obtained by the suspension quantitative sampling method and the microcarrier quantitative sampling method in Example 3 of the present invention compared to the actual situation.

The results are shown in FIG. 9. The results show that the three samples from the microcarrier quantitative sampling method are more reproducible (less variance) and closer to the actual totals.

Example 4 Three-Dimensional Microcarrier-Based Cell Recovery Method

The microcarrier used in the example was 3D FloTrix® microcarrier, purchased from Beijing CytoNiche Biotech Ltd., with Catalog No. of CNF-F01T-50.

The adipose mesenchymal stem cell medium used in the example was human mesenchymal stem cell medium (Viraltherapy Technologies Co., Ltd., Catalog No.: M001).

(I) Three-Dimensional Microcarrier-Based Cell Recovery and Static Culture

I. Recovery and Static Culture of Adipose-Derived Mesenchymal Stem Cells

1. Static Culture Vessel and Preparation of Microcarriers

Sterile and dried microcarriers were placed into a culture vessel; The culture vessels available for use were well plates, petri dishes, and the like without adherent treatment. The appropriate size should be selected according to the number of cells to be recovered and attention should be paid to the tightness of the vessel according to the environment required by the cells. The required microcarriers were aseptically taken into the selected culture vessel and ensure that the microcarriers were kept at room temperature and dry until inoculation was completed. For the experiment, one tablet (20 mg) of microcarrier was used in a non-adherent treated 6-well plate.

2. Recovery of Cryopreserved Cells

Cryopreserved adipose-derived MSCs were taken and quickly thawed in a constant temperature water bath at 37° C. When there was no ice, they were quickly transferred to the ultra-clean bench for subsequent routine recovery operations.

3. Transfer of Thawed Cryopreserved Cells

After completion of the step 2, the thawed cells were washed and centrifuged to remove the supernatant, and the cells were resuspended using culture medium to obtain a cell suspension with a cell concentration of preferably 5 to $500 \times 10^5$ cells/mL. In the experiment, the cell concentration in suspension was $1 \times 10^6$ cells/mL.

4. Inoculation

After completion of the step 3, the cell suspension was inoculated into a 6-well plate with microcarriers prepared in the step 1 with a cell to microcarrier ratio of 5 to $100 \times 10^3$ cells/mg and a medium volume to microcarrier ratio of 100 to 400 μL:20 mg. In the experiment, 200 μl of cell suspension ($2 \times 10^5$ cells in total) was inoculated into a 6-well plate prepared in the step 1.

5. Incubation

After completion of the step 4, incubation was required for 20 to 240 minutes, but it is necessary to maintain a suitable environment throughout the incubation process, paying attention to conditions such as temperature, humidity, sterility, gas, etc. A normal incubator for normal cell culture was sufficient. If the incubator did not have a humidity setting, some sterile humectant (PBS, culture medium, distilled water and some other liquid that provides a moist environment but does not affect the cells or benefit them) can be manually added around the inoculated microcarriers. When incubating in a small dish, the small dish can be placed in a larger vessel and a wet box made around the small dish in the larger vessel, similarly for well plates. In the experiment, 6-well plates were chosen to be incubated in a $CO_2$ incubator at 37° C. for 2 hours and 2 ml of PBS was added between the 6-well plates.

6. Medium Replenishment

After completion of the step 5, the replenishment volume was selected according to the number of cells inoculated, the cycle of medium exchange and the type of medium. 1 ml of serum medium was usually sufficient for 620,000 cells for 1 day. In the experiment, 8 ml of medium was replenished.

7. Culture and Recovery

After completion of the step 6, the recovered cells were placed into a suitable culture environment for subsequent cell recovery and culture. In the experiment, the 6-well plates were placed in a 37° C. $CO_2$ incubator for culture.

8. Monitoring

Depending on the needs of the experiment, the cell culture time, the period of medium replenishment and the period of cell status detection could be set. Cell status indicators comprised medium color, microcarrier status, cell staining analysis, cell lysis count, etc. Cells were cultured for a total of 5 days in the experiment, with a medium replenishment on Day 4. Cell detection using the kit was performed on Day 1 and Day 4 after inoculation (step 10) and cell counting was performed on Day 5 (step 11).

9. Fresh Cell Control Group (1) Cryopreserved adipose-derived MSCs were taken and quickly thawed in a constant temperature water bath at 37° C. When there was no ice, they were quickly transferred to the ultra-clean bench for subsequent routine recovery operations. The thawed cells were washed and centrifuged to remove the supernatant, and the cells were resuspended using culture medium to obtain a cell suspension, which was inoculated at a density of 15,000 cells/cm² in a T75 cell culture flask with 15 mL of medium added and cultured for 3 days to grow to full.

(2) After completion of the step (1), the full-grown cells were subjected to conventional cell digestion, centrifuged to remove the supernatant and then used in a medium with a cell concentration of preferably 5 to $500 \times 10^5$ cells/mL. In the experiment, the cell concentration in the cell suspension was $1 \times 10^6$ cells/mL.

(3) After completion of the step (2), the operation followed steps 4 to 8 to inoculate the cells into a 6-well plate containing microcarriers and proceeded with subsequent operations. Cell detection using the kit was performed on Day 1 and Day 4 after inoculation (step 10) and cell counting was performed on Day 5 (step 11).

10. Cell Monitoring
(1) Kit: Live & Dead Viability/Cytotoxicity Assay Kit for Animal Cell, Catalog No.: KGAF001;
(2) 50 to 100 μL of the microcarrier suspension containing the cells was added to a 96-well plate;
(3) The supernatant was removed as much as possible, PBS was added and washed once, PBS was removed as much as possible after 2 minutes, each well was stained by adding 100 μL of the staining solution configured according to the instructions of the kit. After staining for 20 to 30 minutes at room temperature and protected from light, observation was carried out under a fluorescent microscope.

Figure 10:
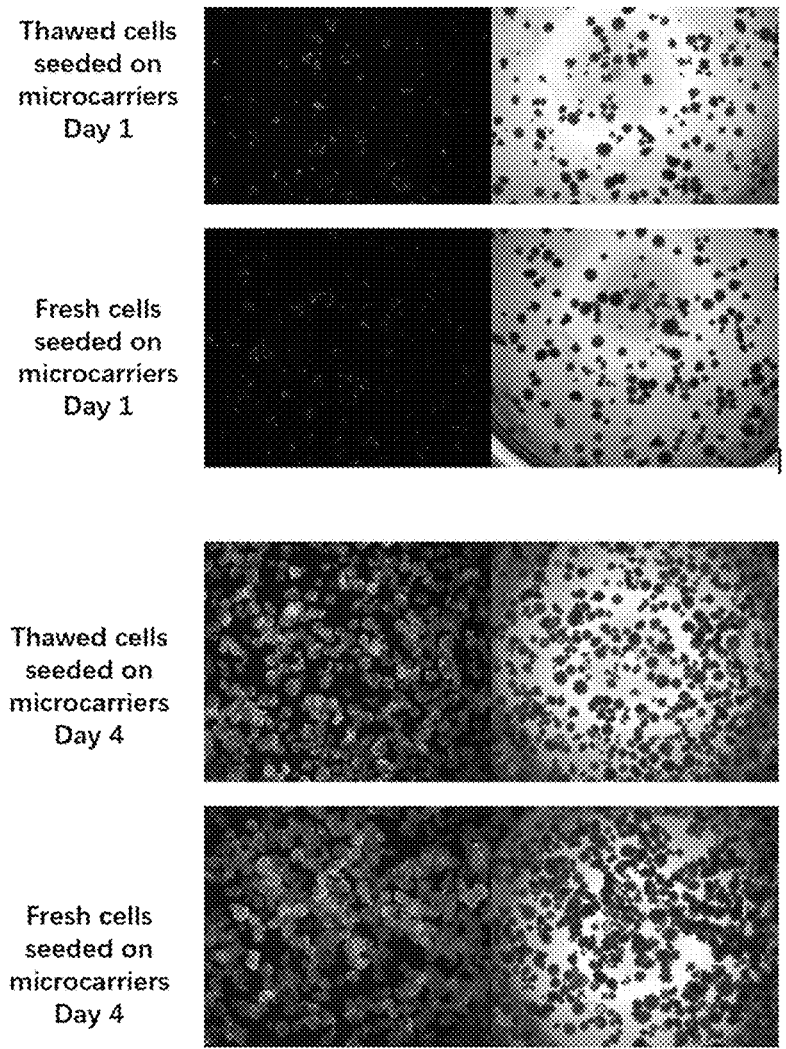
FIG. 10 shows the monitoring results of three-dimensional static recovered cells and control cells in Example 4 of the present invention.

The results are shown in FIG. 10. The results show that cryopreserved adipose-derived MSCs recovered onto microcarriers for static culture ranged from only 1 to 2 cells on each microcarrier sphere at the beginning to more cells on all microcarriers after 4 days, indicating that cryopreserve adipose-derived MSCs can be directly recovered onto microcarriers for static culture, while comparing the number of cells on microspheres inoculated with recovered cells and those inoculated with fresh cells there was almost no difference, indicating that by recovering the cells directly onto the microcarrier, the cell growth is the same as when fresh cells are traditionally obtained from the culture flask and inoculated onto the microcarrier, thus eliminating the need for tedious operations to recover the cells into the culture flask and then digest them to obtain fresh cells for inoculation onto the microcarrier.

11. Cell Counting to Determine Cell Proliferation
On Day 5 of cell culture, the cells were harvested according to the method described in the patent application "A Method for harvesting cells on three-dimensional microcarrier" (Chinese Patent Application No.: 201910101736.0), and counted by means of a cell counting plate.

Figure 11:
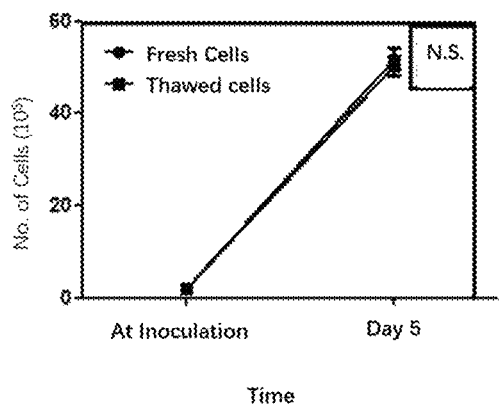
FIG. 11 shows the proliferation of three-dimensional static recovered cells and control cells in Example 4 of the present invention.

The results are shown in FIG. 11. The results show that the number of cells increased from 200,000 at the time of inoculation to 5.027 million when adipose-derived MSCs were recovered to static culture on microcarriers (recovery group) and was not significantly different (p=0.42) from the number of cells (5.187 million) obtained by the conventional post-digestion passaged static culture method (fresh group).

II. Recovery and Static Culture of Adipose-Derived Mesenchymal Stem Cell Microcarriers The cryopreserved adipose-derived MSC microcarriers were prepared according to the method described in the patent application "A Method for In Situ Cell Cryopreservation on Three-Dimensional Microcarrier" (Chinese Application No. 201910097650.5).

1. Static Culture Vessel and Preparation of Microcarriers
Same as step 1 in Part I.
2. Recovery of Cryopreserved Cells
Cryopreserved adipose-derived MSC microcarriers (referred to as adipose-derived MSC microtissues in subsequent descriptions) were taken and rapidly thawed in a constant temperature water bath at 37° C. As microtissues could affect the observation of lysis results, the cryogenic storage tube needed to be tilted and gently shaken during observation, and when there was no ice, they were quickly transferred to the ultra-clean bench for subsequent routine resuscitation operations.

3. Transfer of Thawed Cryopreserved Cells
After completion of the step 2, the thawed cells were washed and centrifuged to remove the supernatant, and the cells were resuspended using culture medium to obtain a cell suspension. In the cell suspension, the concentration of cells in the microtissue was preferably 5 to $500 \times 10^5$ cells/ml. However, the actual microcarrier itself could occupy a large volume, or poor supernatant removal could result in a somewhat larger resuspension volume than expected, which could be scaled to take the required cells when accurate counts were required. For supernatant removal the centrifugal force could be increased and the supernatant pipetted as much as possible, whereas for the microcarriers themselves the volume occupied could be excluded and had little effect on the later experiments.

4. Inoculation
After completion of the step 3, 200 μl of cell suspension was inoculated into a 6-well plate with microcarriers prepared in the step 1.
5. Incubation
Same as step 5 in Part I.
6. Medium Supplementing
Same as step 6 in Part I.
7. Culture and Recovery
Same as step 7 in Part I.
8. Monitoring
Same as step 8 in Part I.
9. Cell Monitoring
Same as step 10 in Part I.

Figure 12:
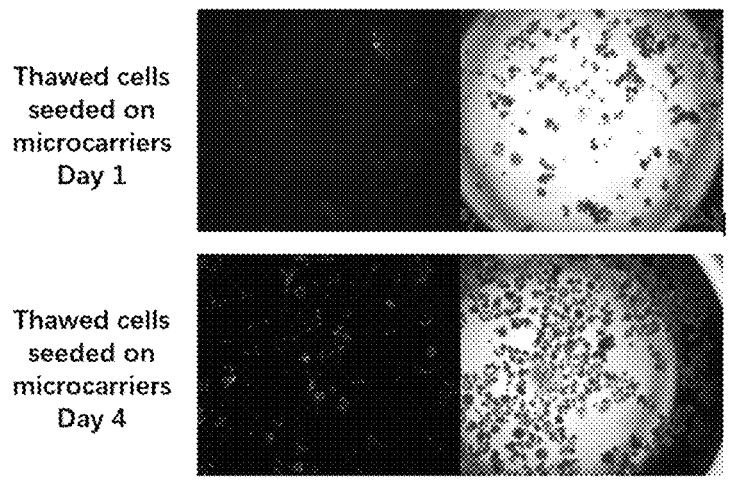
FIG. 12 shows the monitoring results of three-dimensional static recovered cell microstructure in Example 4 of the present invention.

The results are shown in FIG. 12. The results show that the cryopreserved adipose-derived MSC microtissues were recovered onto new microcarriers in static culture. On D1 after recovery, only a small number of microcarriers had many cells on them (bright dots), this was the recovered microtissues and the others with fewer cells were the new microcarriers, while on the fourth day after culture, all microcarriers had cells on them, indicating that the cryopreserved microtissues could be recovered onto the new microcarrier tablets for static culture.

(II) Three-Dimensional Microcarrier-Based Cell Recovery and Dynamic Culture

I. Recovery and Dynamic Culture of Adipose-Derived Mesenchymal Stem Cells

1. Dynamic Culture Vessel and Preparation of Microcarriers
An appropriate amount of microcarriers were placed in a cell culture flask with built-in impeller or in another clean, sterile, endotoxin-free vessel where the microcarriers can be stirred and suspended; the microcarriers were resuspend by adding 0 to 50% (v/v) of the final culture medium and allowed to stand or stir for more than 0 hours (no time limit). In the experiment, 10 tablets of 200 mg microcarrier were added to a 125 mL cell culture flask with built-in impeller containing 10 ml of medium and left to stand for 10 minutes.

2. Recovery of Cryopreserved Cells
Cryopreserved adipose-derived MSCs were taken and quickly thawed in a constant temperature water bath at 37° C. When there was no ice, they were quickly transferred to the ultra-clean bench for subsequent routine recovery operations.

3. Transfer of Thawed Cryopreserved Cells
After completion of the step 2, the thawed cells were washed and centrifuged to remove the supernatant, and the cells were resuspended using culture medium to obtain a cell suspension, the resuspension volume is 1 to 100% (volume percentage) of the medium for the final culture system, at a concentration of 5 to 500×10$^5$ cells/mL. In the experiment, the cell concentration in suspension was 1×10$^6$ cells/mL in a total of 2 mL.

4. Inoculation

After completion of the step 3, the above cell suspension was mixed into the cell culture flask with built-in impeller prepared in the step 1 and mixed with new microcarriers. The ratio of cell to new microcarrier was 5 to 100×10$^3$ cells/mg of microcarrier to be inoculated; after mixing, the cell culture medium was added and the ratio of microcarrier to medium was adjusted to 1 mg:1 to 1000 μL. In the experiment, 2 million recovered cells were inoculated in 200 mg of new microcarriers and the medium was replenished to 60 mL.

The cell culture flask with built-in impeller was placed on a low speed stirrer and placed in an incubator for stirring. Stirring could be done by constant speed stirring or variable speed alternating or variable speed cyclic stirring, stirring direction could be clockwise, counterclockwise or alternating direction stirring to transfer the cells from the seed microcarriers to the new microcarriers, stirring time was 0.1 to 100 hours, and stirring speed was 1 to 200 rpm. In the experiment, the variable speed cyclic clockwise stirring method and the constant speed clockwise stirring method were compared and three sets of experiments were set up as follows:

Group 1 (standing inoculation): a cell culture flask with built-in impeller was placed on a low-speed stirrer and placed in an incubator for 4 hours, then stirred clockwise at 40 rpm for 5 minutes, 20 rpm for 20 minutes in a cycle of variable speed until the 24th hour and then clockwise at a constant speed (60 rpm) until the 96th hour.

Group 2 (intermittent inoculation): a cell culture flask with built-in impeller was placed on a low-speed stirrer and placed in an incubator, cyclic clockwise stirring at 40 rpm for 5 minutes, 20 rpm for 20 minutes in a cycle for 24 hours followed by clockwise stirring at a constant speed (60 rpm) until the 96th hour.

Group 3 (constant speed inoculation): a cell culture flask with built-in impeller was placed on a low speed stirrer and placed in the incubator at a constant speed (60 rpm) clockwise until the 96th hour.

Each group was sampled at the 4th hour for cell detection (step 6).

The culture was continued.

After completion of the step 4, the culture was continued at a constant speed (60 rpm) with clockwise stirring until Day 6. Samples were taken on Day 1, Day 2, Day 3, Day 4, Day 5 and Day 6 for cell counting (step 7).

6. Cell Monitoring (1) Kit: Live & Dead Viability/Cytotoxicity Assay Kit for Animal Cell, Catalog No.: KGAF001;

(2) 50 to 100 μL of microcarrier suspension containing cells was added into a 96-well plate;

(3) The supernatant was removed as much as possible, PBS was added and washed once, PBS was removed as much as possible after 2 minutes, each well was stained by adding 100 μL of the staining solution configured according to the instructions of the kit. After staining for 20 to 30 minutes at room temperature and protected from light, observation was carried out under a fluorescent microscope.

Figure 13:
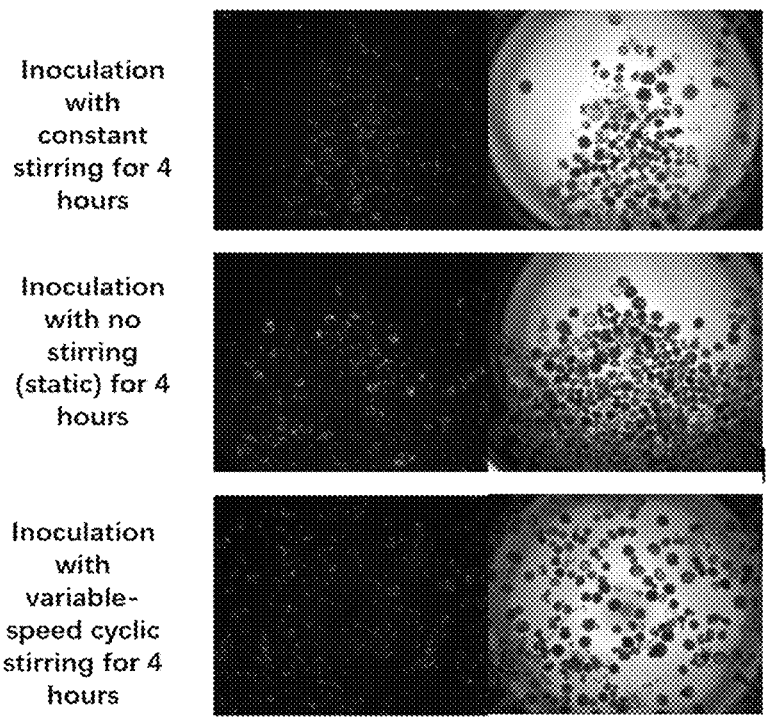
FIG. 13 shows the cell monitoring results of three three-dimensional dynamic recovering cell methods in Example 4 of the present invention.

The results were shown in FIG. 13. The results show that different stirring methods and speed settings during the recovery of cryopreserved adipose-derived MSCs in dynamic culture had an effect on the distribution of cells in the microcarriers, and by comparison the constant speed culture after recovery facilitates the uniform distribution of cells.

7. Cell Counting to Determine Cell Proliferation

After different days of cell inoculation, the cells were harvested according to the method described in the patent application "A Method for harvesting cells on three-dimensional microcarrier" (Chinese Patent Application No.: 201910101736.0), and counted by means of a cell counting plate.

Figure 14:
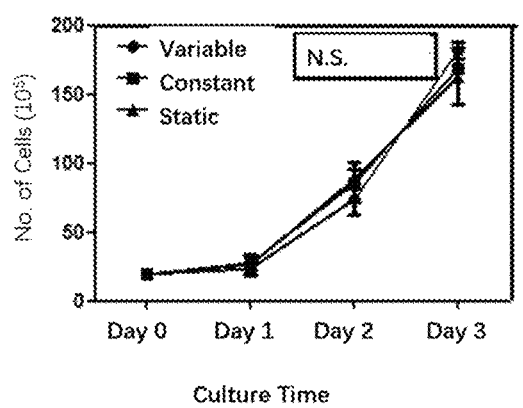
FIG. 14 shows the cell proliferation of three three-dimensional dynamic recovering cell methods in Example 4 of the present invention.

The results are shown in FIG. 14. The results show that cryopreserved cells recovered onto microcarriers proliferated from the initial 2 million to approximately 17.13 million after 3 days culture, and there was no significant difference in the number of cells between these three speed adjustments (groups 1 to 3 in step 4), indicating that the recovery of cryopreserved adipose-derived MSCs onto microcarriers for dynamic culture did not affect the recovery and growth process of the cells regardless of the stirring speed for inoculation (a moderate speed suitable for the cells).

Comparison of Methods

Three-dimensional dynamic recovery cell group: Group 3 in the step 4.

Three-dimensional dynamic fresh cell group: (1) Cryopreserved adipose-derived MSCs were taken and quickly thawed in a constant temperature water bath at 37° C. When there was no ice, they were quickly transferred to the ultra-clean bench for subsequent routine recovery operations. The thawed cells were washed and centrifuged to remove the supernatant, and the cells were resuspended using culture medium to obtain a cell suspension, which was inoculated at a density of 15,000 cells/cm$^2$ in a T75 cell culture flask with 15 mL of medium added and cultured for 3 days to grow to full. (2) After completion of the step (1), the full-grown cells were subjected to conventional cell digestion, centrifuged to remove the supernatant and then used in a medium with a cell concentration of preferably 5 to 500×10$^5$ cells/mL. In the experiment, the cell concentration in the cell suspension was 1×10$^6$ cells/mL. (3) After completion of the step (2), the cell suspension was placed into the prepared cell culture flask with built-in impeller and mixed with the microcarriers after preparing the vessel and microcarriers according to step 1 in Part (II). After mixing, the cell culture medium was added and the ratio of microcarrier to medium was adjusted to 1 mg:1 to 1,000 μL. In the experiment, 2 million fresh cells were inoculated in 200 mg of new microcarriers and the medium was replenished to 60 mL. The culture flask with built-in impeller cell was placed on a low-speed stirrer and placed in an incubator with constant clockwise stirring at 60 rpm until Day 6, and samples were taken on Day 1, Day 2, Day 3, Day 4, Day 5 and Day 6 for cell counting.

Three-dimensional static recovery cell group: three-dimensional static recovery cell group in the step 1 of Part (I).

Three-dimensional static fresh cell group: three-dimensional static fresh cell group in the step 1 of Part (I).

Two-dimensional recovery group: Cryopreserved adipose-derived MSCs were taken and quickly thawed in a constant temperature water bath at 37° C. When there was no ice, they were quickly transferred to the ultra-clean bench for subsequent routine recovery operations. The thawed cells were washed and centrifuged to remove the supernatant, and the cells were resuspended using culture medium to obtain a cell suspension, which was inoculated in 6-well plates at a density of 100,000 cells/well, 4 mL of medium was added and one well was taken for cell counting on Day 1, Day 2, Day 3 and Day 4, respectively.

Two-dimensional passaging group: A T75 full of MSCs was taken, fresh cells were digested from the T75 according to the conventional cell digestion method, the supernatant was removed by centrifugation and the cells were resuspended using culture medium to obtain a cell suspension, which was inoculated in 6-well plates at a density of 100,000 cells/well, 4 mL of medium was added and one well was taken for cell counting on Day 1, Day 2, Day 3 and Day 4, respectively.

Figure 15:
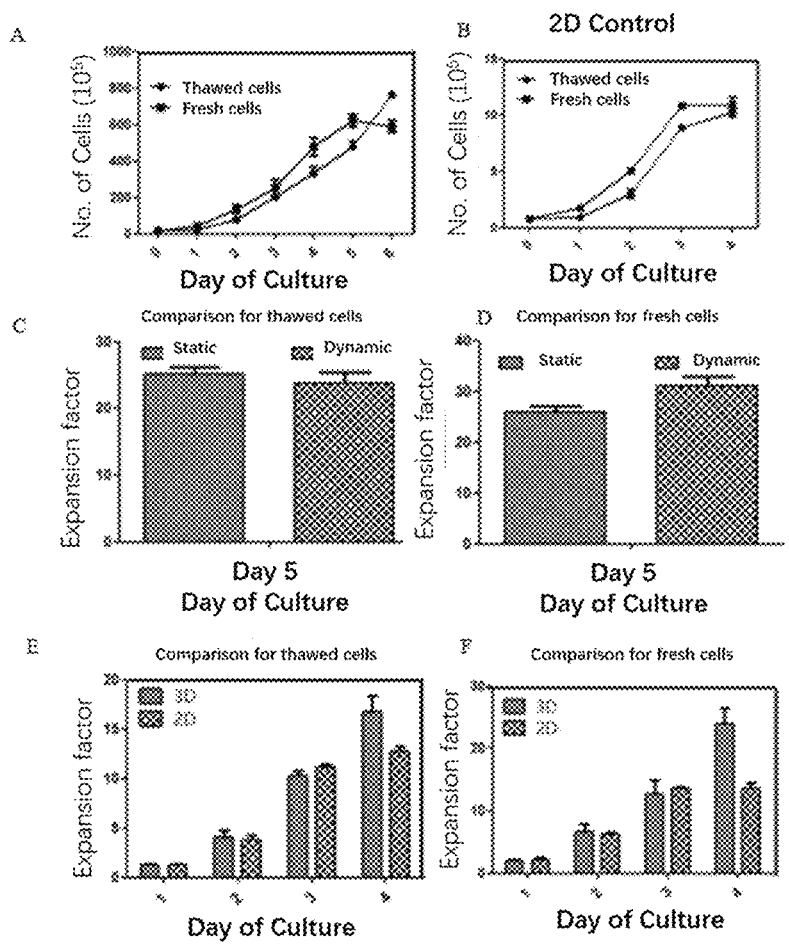
FIG. 15 shows a comparison of the six cell recovery methods in Example 4 of the present invention.

Results are as shown in FIG. 15.

FIG. 15A shows that adipose-derived MSCs were dynamically cultured after recovery to microcarriers, expanding from an initial 2 million recovered cells to 76.33 million after 6 days of culture. Adipose-derived MSCs were recovered to full growth in culture flasks and then passaged to microcarriers for dynamic culture, expanding from an initial 2 million cells to 58.93 million after 6 days of culture. There was no significant difference between the two types of cells in the first 3 days, and the passaged cells grew faster than the recovered cells on Day 4 and Day 5, but the recovered cells outnumbered the passaged cells on Day 6. FIG. 15B shows a 2-dimensional control of the corresponding cells, from which it can be seen that the passaged cells grew slower than the recovered cells in the first 3 days, and by Day 4 both groups of cells were restricted by space and reduced in number, indicating that the recovered cells grew slower. FIG. 15C shows a comparison of the proliferation times of recovered cells inoculated into static and dynamic cultures of microcarriers. There was no significant difference between the two, but the subtle differences indicated that recovered static was slightly slower than recovered dynamic, suggesting that recovered cells were better suited to a moderate stirring speed. FIG. 15D shows that passaged cells were more tolerant to shear forces, and there was no significant difference between the two, which overall indicated that cryopreservation was very damaging to the cells and required some time to recover; FIG. 15E and FIG. 15F both compared cells in dynamic and 2-dimensional culture, and there was no significant difference between the first 3 days, and the 2-dimensional on Day 4 showed significant difference due to space limitation.

II. Recovery and Dynamic Culture of Adipose-Derived Mesenchymal Stem Cell Microcarriers The cryopreserved adipose-derived MSC microcarriers were prepared according to the method described in the patent application "A Method for In Situ Cell Cryopreservation on Three-Dimensional Microcarriers" (Chinese Application No. 201910097650.5).

1. Dynamic Culture Vessel and Preparation of Microcarriers

An appropriate amount of microcarriers were placed in a cell culture flask with built-in impeller or in another clean, sterile, endotoxin-free vessel where the microcarriers can be stirred and suspended; the microcarriers were resuspend by adding 0 to 50% (v/v) of the final culture medium and allowed to stand or stir for more than 0 hours (no time limit). In the experiment, 10 tablets of 200 mg microcarrier were added to a 125 mL cell culture flask with built-in impeller containing 10 ml of medium and left to stand for 10 minutes.

2. Recovery of Cryopreserved Microtissues

Cryopreserved adipose-derived MSC microcarriers (referred to as adipose-derived MSC microtissues in subsequent descriptions) were taken and rapidly thawed in a constant temperature water bath at 37° C. As microtissues could affect the observation of lysis results, the cryogenic storage tube needed to be tilted and gently shaken during observation, and when there was no ice, they were quickly transferred to the ultra-clean bench for subsequent routine resuscitation operations. There were 0.1 to $25 \times 10^6$ cells per mg of microtissue frozen, with a total cell count of 5 to $100 \times 10^3$ cells/mg of microcarriers intended for inoculation. In the experiment there were $0.25 \times 10^6$ cells per mg of microtissues and a total cell count of $2 \times 10^6$ cells.

3. Transfer of Thawed Cryopreserved Cells

After completion of the step 2, the thawed cells were washed and centrifuged to remove the supernatant, and the cells were resuspended using culture medium to obtain a cell suspension, the resuspension volume is 1 to 100% (volume percentage) of the medium for the final culture system, at a concentration of 5 to $500 \times 10^5$ cells/mL. In the experiment, the cell concentration in suspension was $1 \times 10^6$ cells/mL in a total of 2 mL.

4. Inoculation

After completion of the step 3, the above microtissue suspension was mixed into the cell culture flask with built-in impeller prepared in the step 1 and mixed with new microcarriers. The number of cells on the recovered microtissues was 5 to $100 \times 10^3$ cells/mg of new microcarriers; the ratio of microcarrier to medium was adjusted to 1 mg:1 to 1000 μL by adding medium after mixing. in the experiment, 2 million recovered cells were inoculated in 200 mg of new microcarriers and the medium was replenished to 60 mL.

The cell culture flask with built-in impeller was placed on a low speed stirrer and placed in an incubator for stirring. Stirring could be done by constant speed stirring or variable speed alternating or variable speed cyclic stirring, stirring direction could be clockwise, counterclockwise or alternating direction stirring to perform culture. The experiment was performed using 60 rpm clockwise constant speed for 96 hours and then continued at 60 rpm clockwise constant speed for 4 days. Samples were taken on Day 4 for cell detection (step 5) and cell counting (step 6).

5. Cell Monitoring
   (1) Kit: Live & Dead Viability/Cytotoxicity Assay Kit for Animal Cell, Catalog No.: KGAF001;
   (2) 50 to 100 μL of microcarrier suspension containing cells was added into a 96-well plate;
   (3) The supernatant was removed as much as possible, PBS was added and washed once, PBS was removed as much as possible after 2 minutes, each well was stained by adding 100 μL of the staining solution configured according to the instructions of the kit. After staining for 20 to 30 minutes at room temperature and protected from light, observation was carried out under a fluorescent microscope.

Figure 16:
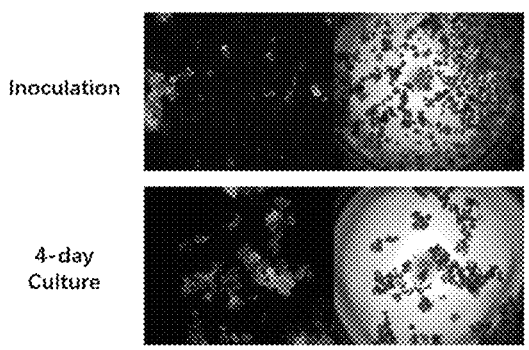
FIG. 16 shows the monitoring results of three-dimensional static recovered cell microstructures in Example 4 of the present invention.

The results are shown in FIG. 16. The results show that when the cryopreserved adipose-derived MSC microcarriers were recovered onto new carriers, they gradually resume expansion from fewer cells at the beginning to more cells on each microcarrier sphere, indicating that the cryopreserved microtissues can be directly recovered onto new carriers.

6. Cell Counting to Determine Cell Proliferation

After different days of cell inoculation, the cells were harvested according to the method described in the patent application "A Method for harvesting cells on three-dimensional microcarrier" (Chinese Patent Application No.: 201910101736.0), and counted by means of a cell counting plate.

Figure 17:
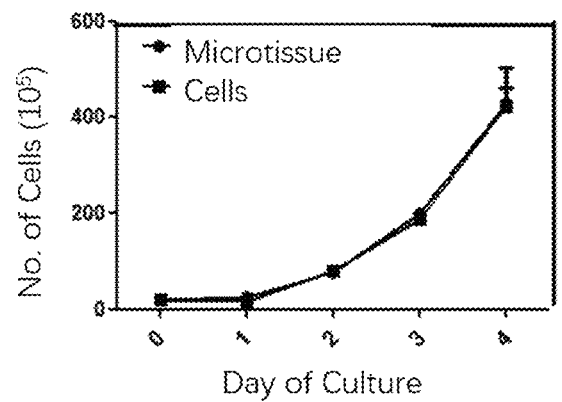
FIG. 17 shows the cell proliferation of three-dimensional dynamic recovered cell microstructures in Example 4 of the present invention.

The results are shown in FIG. 17. The results showed that there was no significant difference between the cryopreserved umbilical cord MSC microtissues after recovery to microcarriers for culture and the cryopreserved cells after recovery and inoculation to microcarriers for culture, with a P value of 0.73. The microtissue group expanded from an initial seed microcarrier with only 2 million cells to 42.82 million after 4 days of culture, indicating that the microtissues were able to be recovered to microcarriers after cryopreservation.

Example 5: Three-Dimensional Microcarrier Cell Culture-Based In Situ Passaging Method The microcarrier used in the example was 3D FloTrix® microcarrier, purchased from Beijing CytoNiche Biotech Ltd., with Catalog No. of CNF-F01T-50.

(I) Static In Situ Passaging Based on Three-Dimensional Microcarrier Cell Culture Test cells: adipose-derived MSCs and umbilical cord MSCs.

I. Static In Situ Passaging Method

1. Preparation of New Microcarriers

Sterile and dried microcarriers were placed into a culture vessel; in the embodiment, 20 mg of microcarriers were used in a 6-well plate.

2. Preparation of Seed Microcarrier Suspension

Seed microcarriers were microcarriers cultured with test cells. The seed microcarriers were cultured according to patent application No. 201910098003.6 (A Method of Cell Attachment Culture on Three-Dimensional Microcarrier). Microcarriers with a cell density of 10,000-1,000,000 cells/mg microcarrier were used as seed microcarriers and the seed microcarriers were resuspended to 0.1 to 50 mg/mL (i.e. 0.5 to 25 million cells/mL volume) using cell culture medium.

Wherein, for adipose-derived MSCs: a cell density of 500,000 cells/mg microcarriers, and a resuspension density of 5 mg/mL; for umbilical cord MSCs: a cell density of 120,000 cells/mg microcarriers, and a resuspension density of 15 mg/mL.

3. Inoculation

After mixing well the seed microcarrier suspension prepared in the step 2 above, an appropriate amount of the seed microcarrier suspension was pipetted and added dropwise to the 6-well plate prepared in the step 1 containing 20 mg of new microcarriers, so that the seed microcarrier suspension was well mixed with the new microcarriers; the ratio of seed microcarrier to new microcarrier was 0.0002 to 200 mg seed microcarriers/mg new microcarriers. The mixed microcarriers were incubated in an incubator for an appropriate time, which could be 0.5 to 24 hours, specifically 2 hours or 24 hours; the cells on the seed microcarriers were allowed to pass onto the new microcarriers.

Wherein, for adipose-derived MSCs: 1 mg of seed microcarriers inoculated into 20 mg of new microcarriers; for umbilical cord MSCs: 3 mg of seed microcarrier suspension inoculated into 20 mg of microcarriers; both groups of cells were incubated in the incubator for 2 hours.

4. Culture: After incubation, cell culture was continued by adding cell culture medium according to conventional cell culture methods, then static in situ passaging was completed.

II. Control Experiment

For control experiment, cells were digested and then inoculated onto the microcarriers for passaging, i.e. the cells on the seed microcarriers were digested and collected (according to patent application No. 201910101736.0, "A method for harvesting cells on three-dimensional microcarrier"), and then resuspended into cell-only suspension, which was mixed with 20 mg of microcarriers at the same cell concentration and inoculation volume as in the step 3, incubated equally for 2 hours and then added to the cell culture medium for further incubation.

III. Results

1. Cell Observation
   (1) Kit: Live & Dead Viability/Cytotoxicity Assay Kit for Animal Cell, Catalog No.: KGAF001;
   (2) 50 to 100 µL of the microcarrier suspension containing the cells was added to a 96-well plate;
   (3) The supernatant was removed as much as possible, PBS was added and washed once, PBS was removed as much as possible after 2 minutes, each well was stained by adding 100 µL of the staining solution configured according to the instructions of the kit. After staining for 20 to 30 minutes at room temperature and protected from light, observation was carried out under a fluorescent microscope.

Figure 18:
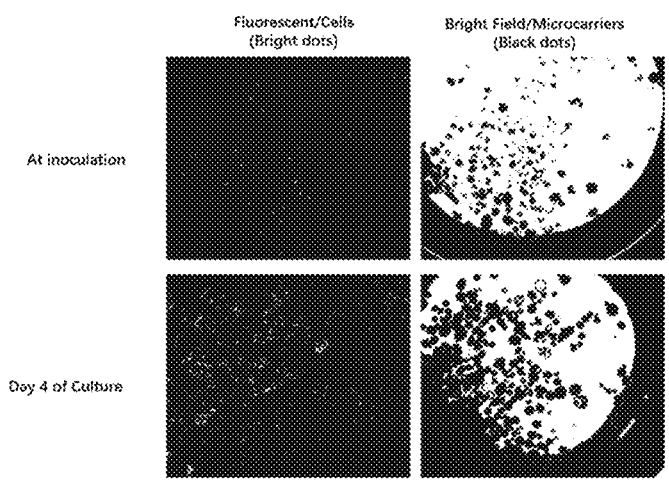
FIG. 18 shows that when the adipose-derived MSCs were inoculated by the static in situ passaging method, only a few of microcarriers had cells on them (bright dots), whereas on Day 4 after in situ passaging culture, cells were present on all microcarriers in Example 4 of the present invention.

Result Analysis:

FIG. 18 shows that when adipose-derived MSCs were inoculated by the static in situ passaging method, only a small number of microcarriers had cells on them (highlight), which were the seed microcarriers and the others without cells were the new microcarriers, while on Day 4 after in situ passaging culture, all microcarriers had cells on them, indicating that the cells on the seed microcarriers could be transferred to the new microcarriers and proliferate.

Figure 19:
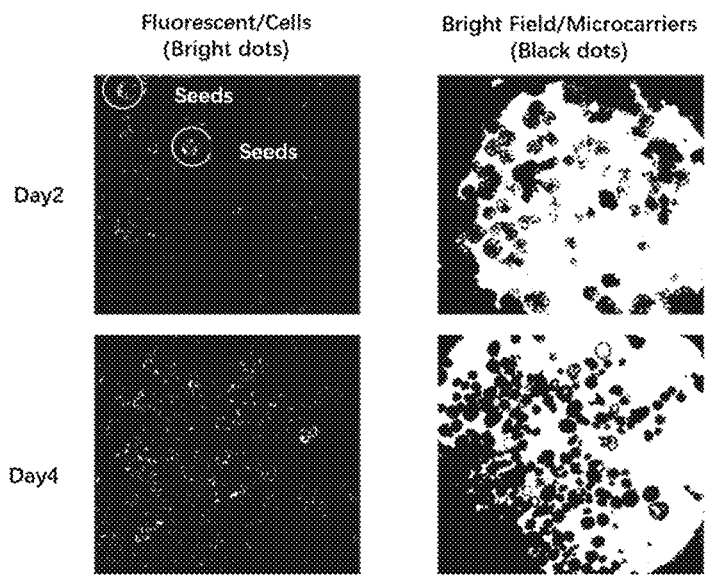
FIG. 19 shows that on Day 2 after umbilical cord MSCs were inoculated by the static in situ passaging method, only a few microcarriers had many cells on them (bright dots), whereas on Day 4 after in situ passaging culture, cells were present on all microcarriers in Example 5 of the present invention.

FIG. 19 shows that on Day 2 after inoculation by static in situ passaging, only a small number of microcarriers had many cells on them (bright dots), which were the seed microcarriers and the others with few cells were the new microcarriers, while on Day 4 after in situ passaging culture, all microcarriers had cells on them, indicating that the cells on the seed microcarriers could be transferred to the new microcarriers and proliferate.

2. Cell Counting to Determine Whether Cells have Completed Passage Expansion

Performed in accordance with the patent application "A Method for Harvesting Cells on Three-dimensional microcarrier" (application No. 201910101736.0).

After 4 days of incubation, 20 mg of cell-grown microcarriers were transferred from the culture well plate to a centrifuge tube, centrifuged at 400×g for 2 minutes, the supernatant was pipetted, an appropriate amount of PBS was added, shaken gently by hand for 20 to 30 seconds, the supernatant was pipetted as much as possible, and the PBS wash was repeated once; 3 mL of lysis solution (lysis solution formulation: 0.1% collagenase, 0.1% ethylene diamine tetraacetic acid, 0.05% Trypsin; % indicated g/100 mL) was added, and incubated in an incubator for 30 minutes, during which time the cells were gently blown several times with a 1 ml pipette every 10 minutes; after 30 minutes, the microcarrier was completely lysed and 3 mL of whole medium was added to terminate the lysis process; the tube was centrifuged at 200×g for 5 minutes, the supernatant was discarded and the cells were resuspended and counted through a cell counting plate.

Figure 20:
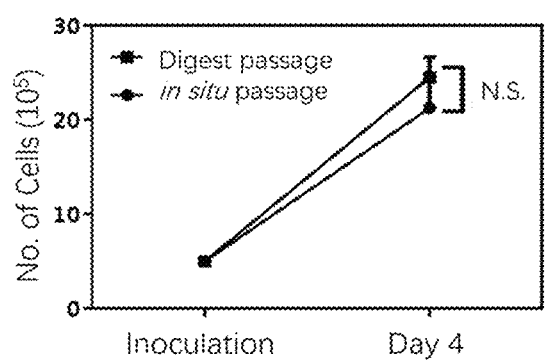
FIG. 20 shows that the number of cells increased from 500,000 at the time of inoculation to 2.1 million after the adipose-derived MSCs were cultured by the static in situ passaging method and was not significantly different (p=0.32) from the number of cells obtained by the conventional post-digestion passaging method (2.4 million) in Example 5 of the present invention.
Figure 21:
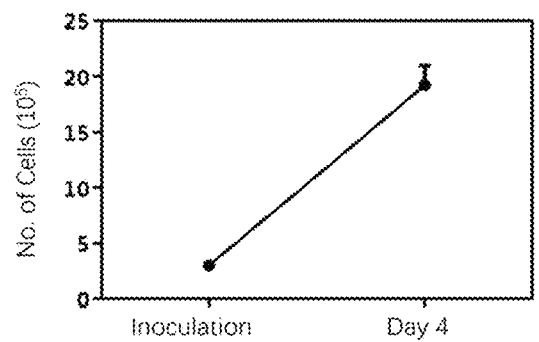
FIG. 21 shows that the number of cells increased from 300,000 at the time of inoculation to 1.9 million after the umbilical cord MSCs were cultured by static in situ passaging methods in Example 5 of the present invention.

Result Analysis:

FIG. 20 shows that the number of adipose-derived MSCs increased from 500,000 at the time of inoculation to 2.1 million cells by the static in situ passaging method and was not significantly different from the number of cells obtained by the conventional post-digestion passaging method (2.4 million) (p=0.32). FIG. 21 shows that the number of umbilical cord MSCs cultured by the static in situ passaging method increased from 300,000 at the time of inoculation to 1.9 million cells, indicating that the cells underwent proliferation and expansion.

(II) Dynamic In Situ Passaging Based on Three-Dimensional Microcarrier Cell Culture Test cells: Adipose-derived MSCs and umbilical cord MSCs.

I. Dynamic In Situ Passaging

1. Preparation of new microcarrier suspension: 200 mg of new microcarrier powder was weighed and poured into a cell culture flask with built-in impeller (Bellco Glass, USA; Catalog No.: 1965-61001; schematic diagram shown in FIG. 1); cell culture medium was added at a ratio of 1 to 2000 µL:1 mg microcarriers and left to stand or stirred for more than 0 hours (not including 0 hours, no time limit).

Wherein, for adipose-derived MSCs: 20 ml of cell culture medium was added for 200 mg of new microcarriers, and left to stand for 14 hours. For umbilical cord MSCs: 10 ml of cell culture medium was added for 100 mg of new microcarriers, and left to stand for 14 hours.

2. Preparation of Seed Microcarrier Suspension

Seed microcarriers were microcarriers cultured with test cells. The seed microcarriers were cultured according to patent application No. 201910098003.6 (A Method of Cell Attachment Culture on Three-Dimensional Microcarrier). Microcarriers with a cell density of 10,000-1,000,000 cells/mg microcarrier (e.g. 100,000-500,000 cells/mg microcarrier) were used as seed microcarriers and the seed microcarriers were resuspended to 0.1 to 50 mg/mL (i.e. 0.5 to 25 million cells/mL volume).

Wherein, for adipose-derived MSCs: seed microcarriers with a cell density of 500,000/mg and a resuspension density of 1 mg/mL. For umbilical cord MSCs: seed microcarriers with a cell density of 150,000/mg and a resuspension density of 1 mg/mL.

3. Inoculation

The seed microcarrier suspension prepared in the step 2 above was mixed into the cell culture flask with built-in impeller in the step 1, and mixed well with the new microcarrier suspension; the ratio of seed microcarrier to new microcarrier was 0.0002 to 200 mg seed microcarriers/mg new microcarriers; the cell medium was added to adjust the ratio of microcarrier to culture medium to 1 mg:1-1000 µL.

Wherein, for adipose-derived MSCs: 4 mg of seed microcarriers (2 million cells in total) were used to inoculate in 200 mg of new microcarriers and the cell culture medium was replenished to 60 mL. For umbilical cord MSCs: 6.7 mg of seed microcarriers (1 million cells in total) were used to inoculate in 100 mg of new microcarriers and the cell culture medium was replenished to 60 mL.

The cell culture flask with built-in impeller was placed on a low speed stirrer (3D FloTrix® miniSpin low-speed stirrer, Beijing CytoNiche Biotech Ltd., Catalog No.: 3D FTmS-2-2) and placed in an incubator for stirring. Stirring could be done by constant speed stirring or variable speed alternating or variable speed cyclic stirring, stirring direction could be clockwise, counterclockwise or alternating direction stirring to transfer the cells from the seed microcarriers to the new microcarriers, stirring time was 0.1 to 100 hours.

Wherein, for both MSCs a variable speed cyclic clockwise stirring method was used, specifically 60 rmp for 5 minutes and 20 rpm for 20 minutes in a cycle for a total of 24 hours.

4. Culture

After inoculation, the culture could be continued with stirring until expansion effect was achieved.

II. Control Experiment

Control experiment was performed with adipose-derived MSCs, which were digested and then inoculated onto microcarriers for passaging, i.e. the cells on the seed microcarriers were digested and collected (according to patent application No. 201910101736.0, "A method for harvesting cells on three-dimensional microcarrier"), and then resuspended into cell-only suspension. 2 million cells were resuspended in 4 mL and inoculated in 200 mg of new microcarriers in a cell culture flask with built-in impeller and the cell culture medium was replenished to 60 mL. The cell culture flask with built-in impeller was placed on a low-speed stirrer (3D FloTrix® miniSpin low-speed stirrer, Beijing CytoNiche Biotech Ltd., Catalog No.: 3 FTmS-2-2) and placed in an incubator for 24 hours at 60 rmp for 5 minutes and 20 rpm for 20 minutes, specifically, and then the stirring culture was continued until the expansion effect was achieved.

III. Results

1. Cells Observation:
   (1) Kit: Live & Dead Viability/Cytotoxicity Assay Kit for Animal Cell, Catalog No.: KGAF001;
   (2) 50 to 100 µL of the microcarrier suspension containing the cells was added to a 96-well plate;
   (3) The supernatant was removed as much as possible, PBS was added and washed once, PBS was removed as much as possible after 2 minutes, each well was stained by adding 100 µL of the staining solution configured according to the instructions of the kit. After staining for 20 to 30 minutes at room temperature and protected from light, observation was carried out under a fluorescent microscope.

Figure 22:
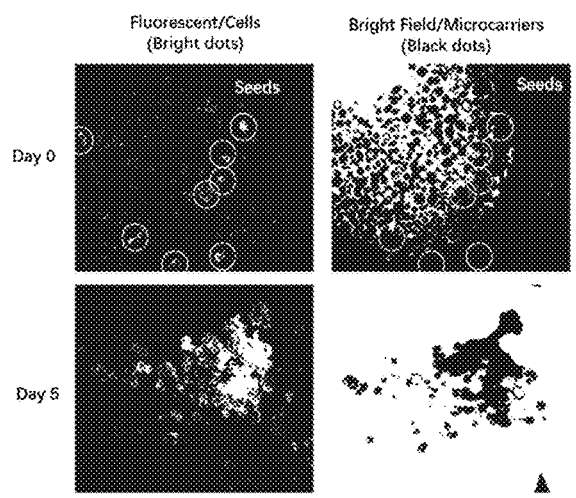
FIG. 22 shows that on Day 2 after adipose-derived MSCs were inoculated by the dynamic in situ passaging method, only a few microcarriers had many cells on them (bright dots), whereas on Day 5 after in situ passaging culture, cells were present on all microcarriers in Example 5 of the present invention.
Figure 23:
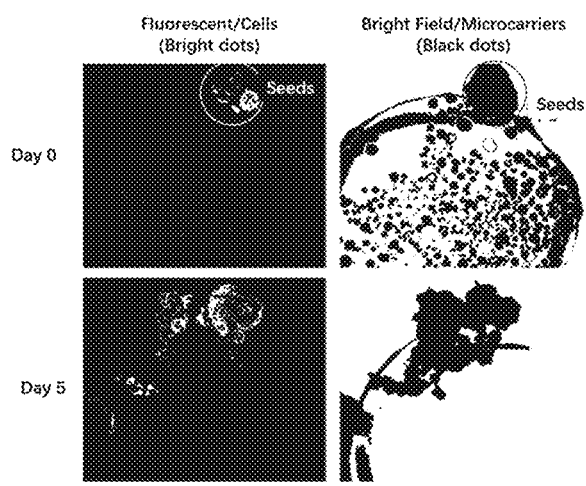
FIG. 23 shows that when the umbilical cord MSCs were inoculated by the dynamic in situ passaging method, only a few of microcarriers had many cells on them (bright dots), whereas on Day 5 after in situ passaging culture, cells were present on all microcarriers in Example 5 of the present invention.

Result Analysis:

FIG. 22 shows that on Day 2 after inoculation of adipose-derived MSCs by dynamic in situ passaging, only a small number of microcarriers had many cells on them as can be seen in the fluorescence image (bright dots), which were the seed microcarriers, but it was clear from the bright field that there were other microcarriers and the others with few cells were the new microcarriers, proving that some cells were transferred to the new microcarriers by in situ passaging and on Day 5 after in situ passaging, cells were present on all microcarriers, indicating that the cells passed onto the new microcarriers had proliferated and expanded. FIG. 23 shows that when umbilical cord MSCs were inoculated by the dynamic in situ passaging method, only a small number of microcarriers had many cells on them (bright dots) as can be seen in the fluorescent image, which were the seed microcarriers, but it was clear from the bright field that there were other microcarriers and the others without cells were the new microcarriers, and on Day 5 after in situ passaging culture, cells were present on all microcarriers, indicating that the cells on the seed microcarriers could be transferred to the new microcarriers and proliferate and expand.

2. Cell Counting to Determine Whether Cells have Completed Passage Expansion

Performed in accordance with the patent application "A Method for Harvesting Cells on Three-dimensional microcarrier" (application No. 201910101736.0).

On different days after inoculation, 3 mL of the microcarrier suspension was transferred from the flask to a centrifuge tube, centrifuged at 400×g for 2 minutes, the supernatant was pipetted, an appropriate amount of PBS was added, shaken gently by hand for 20 to 30 seconds, the supernatant was pipetted as much as possible, and the PBS wash was repeated once; 3 mL of lysis solution (lysis solution formulation: 0.1% collagenase, 0.1% ethylene diamine tetraacetic acid, 0.05% Trypsin; % indicated g/100 mL) was added, and incubated in a 37° C. incubator for 30 minutes, during which time the cells were gently blown several times with a 1 ml pipette every 10 minutes; after 30 minutes, the microcarrier was completely lysed and 3 mL of whole medium was added to terminate the lysis process; the tube was centrifuged at 200×g for 5 minutes, the supernatant was discarded, and according to the requirements of subsequent applications, the cells were resuspended and counted through a cell counting plate.

Figure 24:
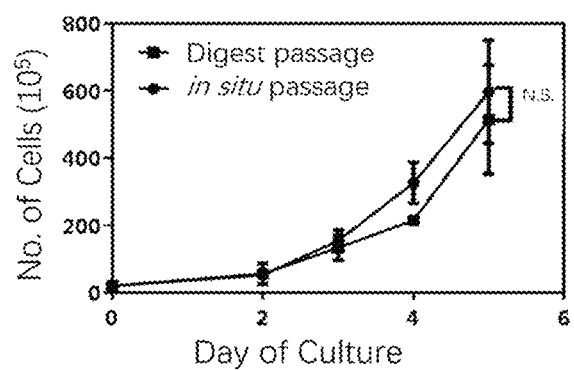
FIG. 24 shows that adipose-derived MSCs can be grown and expanded by dynamic in situ passaging methods, from initially only 2 million cells on seed microcarriers to 50 million after 5 days of culture in Example 5 of the present invention.
Figure 25:
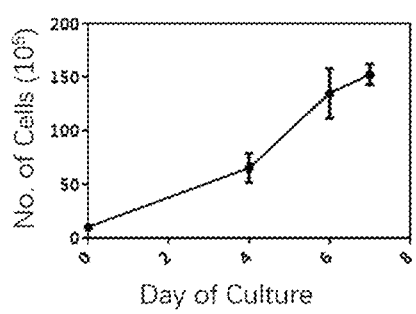
FIG. 25 shows that umbilical cord MSCs can be grown and expanded by dynamic in situ passaging methods, from initially only 1 million cells on seed microcarriers to 15.2 million after 7 days of culture in Example 5 of the present invention.

Result Analysis:

FIG. 24 shows that adipose-derived MSCs could be grown and expanded by the dynamic in situ passaging method, from seed microcarriers with initially only 2 million cells to 59.77 million after 5 days of culture, which was not significantly different from the number of cells obtained by the conventional post-digestion passaging method (51.4 million) (p=0.14). FIG. 25 shows that umbilical cord MSCs could be grown and expanded by the dynamic in situ passaging methods, from seed microcarrier with initially only 1 million cells to 15.2 million after 7 days of culture.

Example 6: Three-Dimensional Microcarrier-Based In Situ Cell Cryopreservation Method I The cells in the section were HEK293T cells, purchased from the Cell Resource Center of Peking Union Medical University, with Catalog No. of CBP60439; the three-dimensional microcarriers were 3D FloTrix® microcarrier, purchased from Beijing CytoNiche Biotech Ltd., with Catalog No. of CNF-F01T-50.

In the example, the three-dimensional microcarrier suspension of cells was prepared according to the following steps.
1. Microcarrier preparation: 200 mg of microcarrier powder was weighed for ultraviolet sterilization and then poured into a sterile cell culture flask with built-in impeller (as shown in FIG. 1); three groups were prepared;
2. Cell preparation: The adipose-derived MSC suspension was prepared in advance, and 5×10$^6$ cells were resuspended in 60 mL complete medium for later use; three groups were prepared;
3. Cell inoculation: The cell suspensions above were mixed into the cell culture flask with built-in impeller, and mixed well with 200 mg of microcarriers;
4. Cell attachment: The cell culture flask with built-in impeller was placed on a low-speed stirrer and placed in a 37° C., 5% $CO_2$ incubator for stirring at 80 rpm to allow the cells to attach to the microcarrier by rotation;
1. The three-dimensional microcarrier suspension containing HEK293T cells was centrifuged at 400×g for 2 minutes and the supernatant was discarded.
2. The cryopreservation solution (90% FBS+10% DMSO) was added and dispensed into cryogenic storage tubes (1 ml of cryopreservation solution contained 10 mg of cell-containing microcarriers, 0.5 to 1 ml per tube).
3. The cryogenic storage tubes were loaded into a cell programmed cooling box and should be placed in a −80° C. refrigerator within 5 minutes and transferred to liquid nitrogen after 24 hours.
4. Recovery of cells attached to microcarriers: For recovery, a 37° C. pre-warmed basal medium was prepared, then the cryogenic storage tubes were quickly placed in a 37° C. water bath, shaken constantly and gently during this time, and when ice sized as one grain of rice remained (about 1 to 2 minutes in the water bath), the tubes were quickly removed from the water bath. Then, the melted three-dimensional microcarrier suspension containing cells was then immediately diluted with the basal medium at a dilution ratio of 1:5, followed by centrifugation at 400×g for 2 minutes, then resuspended for later use.
5. Cell detection method:

(1) In Situ Calcein-AM/PI Staining Method of Living Cells:
 1) Kit: Live & Dead Viability/Cytotoxicity Assay Kit for Animal Cell, Catalog No.: KGAF001;
 2) 50 to 100 µl of the three-dimensional microcarrier suspension containing cells before cryopreservation or recovered after cryopreservation were added to a 96-well plate, respectively;
 3) The supernatant was removed as much as possible, PBS was added and washed once, PBS was removed as much as possible after 2 minutes, each well was stained by adding 100 µL of the staining solution configured according to the instructions of the kit. After staining for 20 to 30 minutes at room temperature and protected from light, observation was carried out under a fluorescent microscope; the results are shown in FIG. 26.

Figure 26:
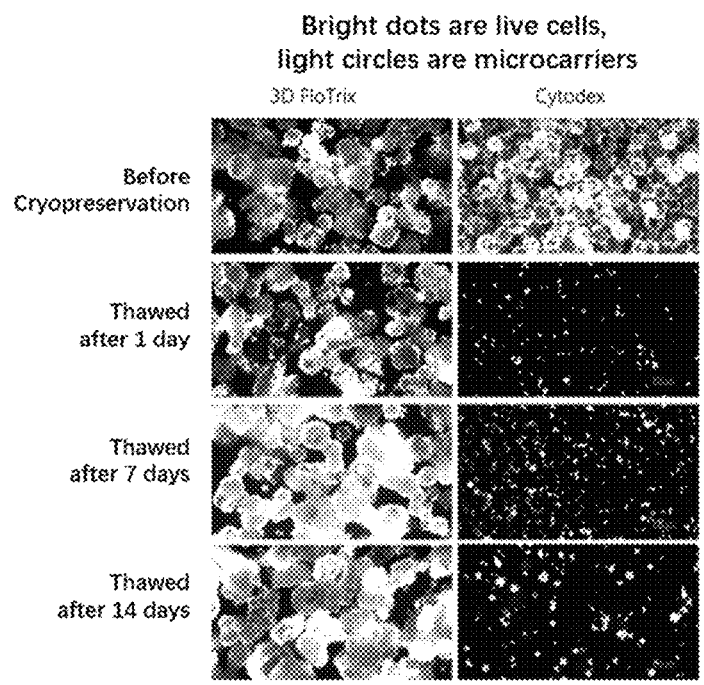
FIG. 26 shows a graph of the recovery results of in situ cryopreserved HEK293 cells on microcarriers after different cryopreservation times in Example 6 of the present invention.

As can be seen from FIG. 26, live cells were stained with the staining solution and could be observed to glow by fluorescence and the cells that glow were the live cells. The illuminated spherical microcarriers proved that the living cells were still attached to the microcarriers. FIG. 26A demonstrates that live cells could be cryopreserved in situ and recovered on 3D FloTrix® microcarriers, even successfully after 2 weeks of cryopreservation. However, in FIG. 26B, after the competitor microcarriers (GE Cytodex, Catalog No.: 17-1271-01, purchased from Beijing Think-Far Technology Co., Ltd.) were cryopreserved and recovered, it could be seen that the cells were detached from the microcarrier and by fluorescence observation it was found that the cells did not attach to the microcarriers but became dotted and scattered in the liquid.

(2) Analytical Method for Detecting Apoptosis Rate by Flow Cytometry:
 1) Cell collection: 20 mg of three-dimensional microcarrier suspension containing cells was centrifuged at 400×g for 2 minutes, and the supernatant was discarded. 3 mL of 0.1% Collagenase Type IV solution (1 g of Collagenase Type IV (Gibco, 17104019) dissolved in 1 L of PBS) was added, and the solution was incubated in a cell incubator at 37° C. for 30 minutes, and centrifuged at 400×g for 5 minutes, and the supernatant was discarded.
 2) Cell washing: The cells were resuspended once by precooled PBS at 4° C. and centrifuged at 400×g for 5 minutes, then the cells were washed.
 3) Cell staining: Cells were stained using Annexin V-FITC/PI Apoptosis Detection Kit (HaiGene Biotech Co., Ltd, S0185), that is, 300 μL of Binding Buffer was added, followed by 5 μL of Annexin V-FITC, mixed and incubated for 15 minutes at room temperature, protected from light; 5 μL of PI was then added for staining for 5 minutes; supplemented with 200 μL of Binding Buffer.
4) Cell flow cytometry: Flow cytometry of the stained cells was performed using BD FACSAria II Flow Cytometer and a report of the cell classification analysis was generated by the instrument.
5) Interpretation of the cell flow cytometry report:
A) Annexin-V negative-PI-negative represents normal cells, i.e. the lower left group in the four-frame cell classification diagram, whose proportion of cells is the proportion of live cells.
B) Annexin-V positive-PI-negative represents cells in the early stages of apoptosis, i.e. the lower right group in the four-frame cell classification diagram, whose proportion of cells is the proportion of cells in the early stages of apoptosis.
C) Annexin-V positive-PI positive represents cells in the later stage of apoptosis or necrotic cells, i.e. the upper right group in the four-frame cell classification diagram, whose proportion of cells is the proportion of cells in the later stage of apoptosis.

Figure 27:
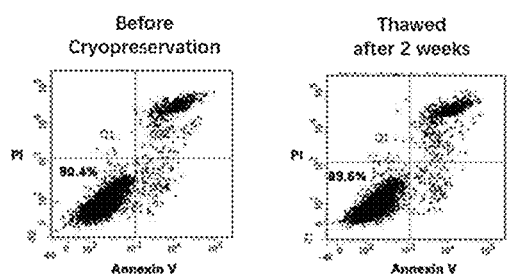
FIG. 27 shows a graph of the results of proportion of living cells before cryopreservation and those recovered after cryopreservation for HEK293 cells on microcarriers in Example 6 of the present invention.

FIG. 27 shows that the percentage of viable cells on 3D FloTrix® microcarriers before cryopreservation was 90.4%; whereas the percentage of viable cells after cryopreservation and then recovery was 89.6%, with a decrease of just under 1%, thus the cells on 3D FloTrix® microcarriers used in the present invention can be preserved in situ with the microcarriers and maintain their activity after recovery.

Figure 28:
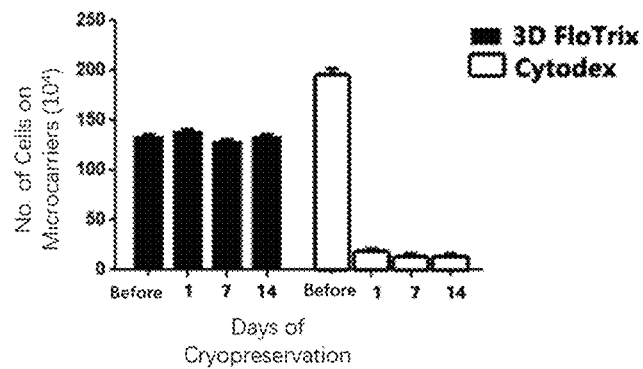
FIG. 28 shows a histogram of the number of HEK293 cells on 3D FloTrix® microcarriers and competitor microcarriers (GE Cytodex) after cryopreservation and recovery in Example 6 of the present invention.

(3) In-Situ Cell Counting Method:
1) Microcarrier collection: 20 mg of the three-dimensional microcarrier suspension containing cells were collected through a 70 μm cell sieve and washed once with PBS to wash off any cells not attached to the microcarriers. The microcarrier suspension containing the cells was then centrifuged at 1500 rpm for 2 minutes and the supernatant was discarded.
2) Cell counting: 3 mL of 0.1% crystal violet solution (0.1 g of crystalline violet, 2.1 g of citric acid, 20 μL of Tween-80, 100 ml of deionized water) at 37° C. for 2 to 5 hours, and the cells were counted with a cell counting plate.
3) Result analysis: The results in FIG. 28 show that after cryopreservation and recovery, the number of cells on the 3D FloTrix® microcarriers remained consistent with that before cryopreservation, while the number of cells on the competitor microcarriers (GE Cytodex, Catalog No.: 17-1271-01, purchased from Beijing Think-Far Technology Co., Ltd.) was greatly reduced due to the rupture of the microcarriers and the scattering of cells; therefore, in the present invention, the use of 3D FloTrix® microcarriers for cell culture followed by cryopreservation and then recovery allows for in situ three-dimensional cell freezing, maintaining the entire chain of cell culture and preservation processes in a three-dimensional environment.

II.

The cells in the section were AD-MSC cells (from School of Medicine, Tsinghua University); the three-dimensional microcarrier was 3D FloTrix® microcarrier, purchased from Beijing CytoNiche Biotech Ltd., with Catalog No. of CNF-F01T-50

1. The three-dimensional microcarrier suspension containing AD-MSC cells was centrifuged at 400×g for 2 minutes and the supernatant was discarded.
2. The cryopreservation solution (90% FBS+10% DMSO) was added and dispensed into cryogenic storage tubes (1 ml of cryopreservation solution contained 10 mg of cell-containing microcarriers, 0.5 to 1 ml per tube).
3. The cryogenic storage tubes were loaded into a cell programmed cooling box and should be placed in a −80° C. refrigerator within 5 minutes and transferred to liquid nitrogen after 24 hours.
4. Recovery of cells attached to microcarriers: For recovery, a 37° C. pre-warmed basal medium was prepared, then the cryogenic storage tubes were quickly placed in a 37° C. water bath, shaken constantly and gently during this time, and when ice sized as one grain of rice remained (about 1 to 2 minutes in the water bath), the tubes were quickly removed from the water bath. Then, the melted three-dimensional microcarrier suspension containing cells was then immediately diluted with the basal medium at a dilution ratio of 1:5, followed by centrifugation at 400×g for 2 minutes, then resuspended for later use.
5. Cell detection method:
(1) In Situ Calcein-AM/PI Staining Method of Living Cells:
1) Kit: Live & Dead Viability/Cytotoxicity Assay Kit for Animal Cells, Catalog No.: KGAF001;
2) 50 to 100 μl of the three-dimensional microcarrier suspension containing cells before cryopreservation or recovered after cryopreservation were added to a 96-well plate, respectively;
3) The supernatant was removed as much as possible, PBS was added and washed once, PBS was removed as much as possible after 2 minutes, each well was stained by adding 100 μL of the staining solution configured according to the instructions of the kit. After staining for 20 to 30 minutes at room temperature and protected from light, observation was carried out under a fluorescent microscope; the results are shown in FIG. 29.

Figure 29:
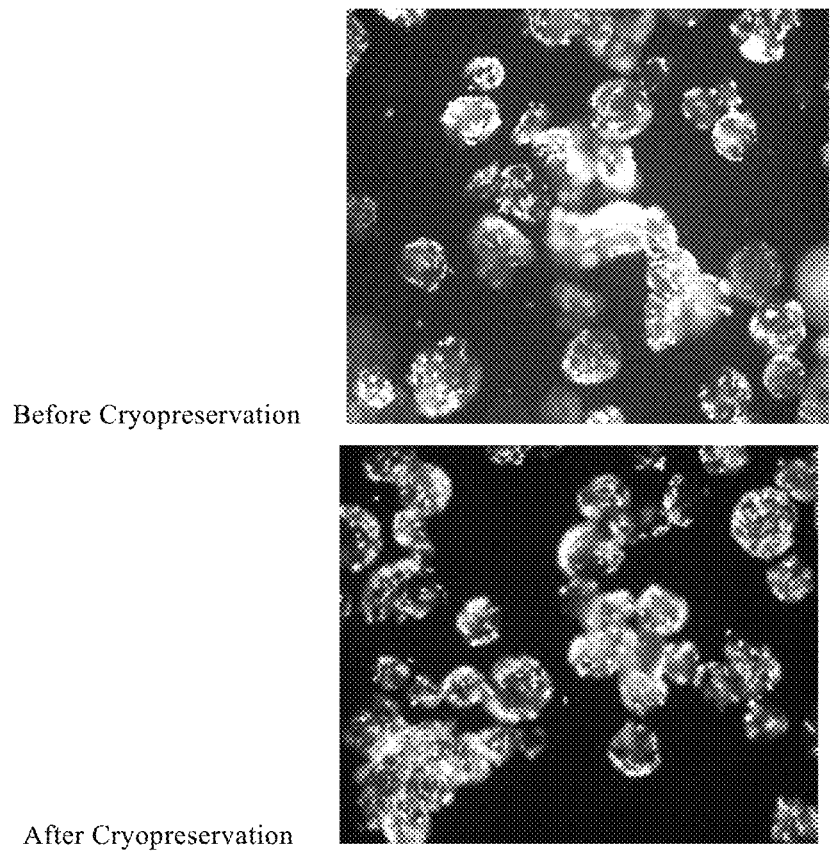
FIG. 29 shows a graph of the recovery results of in situ cryopreserved AD-MSCs on microcarriers after different cryopreservation times in Example 6 of the present invention.

As can be seen from FIG. 29, live cells were stained with the staining solution and could be observed to glow by fluorescence and the cells that glow were the live cells. The illuminated spherical microcarriers proved that the living cells were still attached to the microcarriers. FIG. 29 shows the recovery results of AD-MSC after 1 to 2 days of cryopreservation on 3D FloTrix® microcarriers, with the luminescent live cells still adhering to the microcarriers, indicating that 3D FloTrix® assists in cryopreservation of MSCs.

Figure 30:
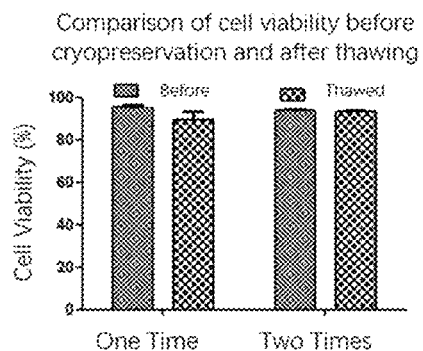
FIG. 30 shows a comparison of the activity of AD-MSCs before and after cryopreservation in Example 6 of the present invention.

FIG. 30 shows that MSCs on 3D FloTrix® microcarriers had a live cell ratio of over 90% before and after cryopreservation, and the difference in cell activity before and after cryopreservation was not significant. Therefore, the MSCs on the 3D FloTrix® microcarriers used in the present invention can be preserved in situ with the microcarriers and maintain their activity after recovery.

(3) Lysis Cell Counting Method:
1) Microcarrier collection: 20 mg of the three-dimensional microcarrier suspension containing cells were collected through a 70 μm cell sieve and washed once with PBS to wash off any cells not attached to the microcarriers. The microcarrier suspension containing the cells was then centrifuged at 1500 rpm for 2 minutes and the supernatant was discarded.
2) Cell counting: 3 mL of lysis solution (lysis solution formulation: 0.1% collagenase, 0.1% ethylene diamine tetraacetic acid, 0.05% Trypsin; % indicated g/100 mL)

was added, and incubated in an incubator for 30 minutes, during which time the cells were gently blown several times with a 1 ml pipette every 10 minutes; after 30 minutes, the microcarrier was completely lysed and 3 mL of whole medium was added to terminate the lysis process; the tube was centrifuged at 200×g for 5 minutes, the supernatant was discarded and the cells were resuspended and counted through a cell counting plate.

Figure 31:
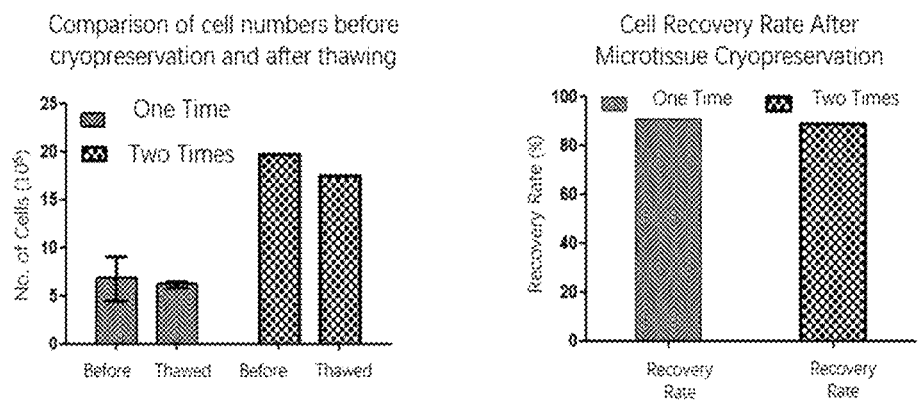
FIG. 31 shows the statistics of the number of cells before and after cryopreservation and the cell recovery rate after cryopreservation of AD-MSCs in Example 6 of the present invention.

3) Result analysis: The results in FIG. 31 show that after cryopreservation and recovery, the number of cells on the 3D FloTrix® microcarriers remained consistent with that before cryopreservation. Therefore, in the present invention, the use of 3D FloTrix® microcarriers for MSC culture allows for long periods of cryopreservation, maintaining the entire chain of cell culture and preservation in a three-dimensional environment.

Figure 33:
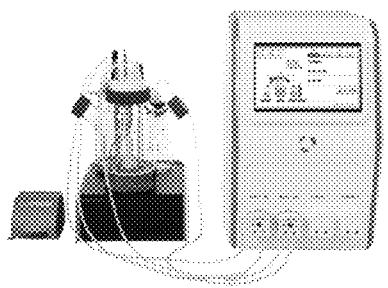
FIG. 33 shows the automated bioreactor (3D vivaSPIN V1, Beijing CytoNiche Biotech Ltd.) used in the first part of Example 7 of the present invention.

Example 7: Large-Scale Expansion of Stem Cells Using Three-Dimensional Culture Method I. Continuous Cell Expansion Culture in Stirred Bioreactor
1. Ten tablets (a total of 200 mg) of 3D TableTrix microcarriers (Beijing CytoNiche Biotech Ltd.; Catalog No.: F01-100) were placed in a cell culture flask with built-in impeller (Bellco Glass, USA; Catalog No.: 1965-61001) and 10 ml of cell culture medium was added.
2. 50 mL of adipose-derived MSC cell suspension (containing 2 million cells) was inoculated into the cell culture flask with built-in impeller containing the microcarriers prepared in step 1.
3. The cell culture flask with built-in impeller from the step 2 were placed on a 3D FloTrix® miniSpin small-scale bioreactor (Beijing CytoNiche Biotech Ltd.; 3D miniSPIN M1) in a cell culture incubator and incubated at a constant speed of 60 rpm clockwise for 6 days (supplemented with 60 mL of fresh medium on Day 3). Cell sampling and counting were carried out daily to obtain data on cell expansion curves. On Day 6, microtissues (i.e. microcarriers containing cells) containing 20 million cells from the cell culture flask with built-in impeller were resuspended in 50 mL of fresh medium using an electric pipette, transferred to a 3D FloTrix® vivaSpin bioreactor ((Beijing CytoNiche Biotech Ltd.; 3D vivaSPIN V1, FIG. 33), and 50 tablets (a total of 1 g) of 3D TableTrix microcarriers (Beijing CytoNiche Biotech Ltd.; Catalog No.: F01-100), which had been previously resuspended (left to stand for 0 to 30 minutes) in 50 mL of medium, were added. The cells were sampled and counted daily to obtain data on cell expansion curves, and cell activity was also measured.

The process parameters set for the 3D FloTrix® vivaSpin bioreactor were controlled as follows: active pumping of 12 ccm of 5% $CO_2$ throughout the process, and a temperature of 37° C. 800 mL of complete medium was actively pumped in at a rate of 10 mL/min at T=0 hour, 500 mL of liquid was actively pumped out at a rate of 10 mL/min followed by 500 mL of fresh medium pumped in at a rate of 10 mL/min at T=96 hour, 500 mL of liquid was actively pumped out at a rate of 10 mL/min followed by 50 tablets of 3D Table Trix™ microcarriers resuspended in 500 mL of fresh medium actively pumped into the reactor at 10 mL/min at T=144 hours. The stirring rates for T=0 to 12 hour and T=144 to 156 hour were variable speeds in cycles of 40 rpm for 5 minutes, 20 rpm for 20 minutes and a constant speed of 60 rpm for the rest of the time.

Cell sampling and counting method: All samples were taken by pipetted 1 mL of sample×3 replicates through the sampler of the 3D FloTrix® vivaSpin bioreactor and transferred to centrifuge tubes, centrifuged at 400×g for 2 minutes, the supernatant was pipetted. 1 mL of lysis solution (lysis solution formulation: 0.1% collagenase, 0.1% ethylene diamine tetraacetic acid, 0.05% Trypsin; % indicated g/100 mL) was added, and incubated in an incubator for 30 minutes until the microcarriers were completely lysed (during which time the cells were gently blown several times with a 1 ml pipette every 10 minutes) and 1 mL of whole medium was added to terminate the lysis process; centrifuged at 200×g for 5 minutes, the supernatant was discard, the cells were suspended and counted through a cell counting plate.

Cell activity assay: 50 μL of cell suspension was mixed with 50 μL of 0.2% Trypan Blue staining solution and an appropriate amount of cells was taken for counting. Either an automated cell counter (e.g. Countstar® BioTech, Shanghai Ruiyu Biotech Co., Ltd.) or a cell counting plate can be used. The number of cells that were crystal clear and the number of cells that were stained blue were recorded separately and the number of cells in the cell suspension was extrapolated from the corresponding dilution ratio.

Cell activity ratio (%)=Number of unstained cells/ (Number of unstained cells+Number of cells stained blue)×100%.

Figure 32:
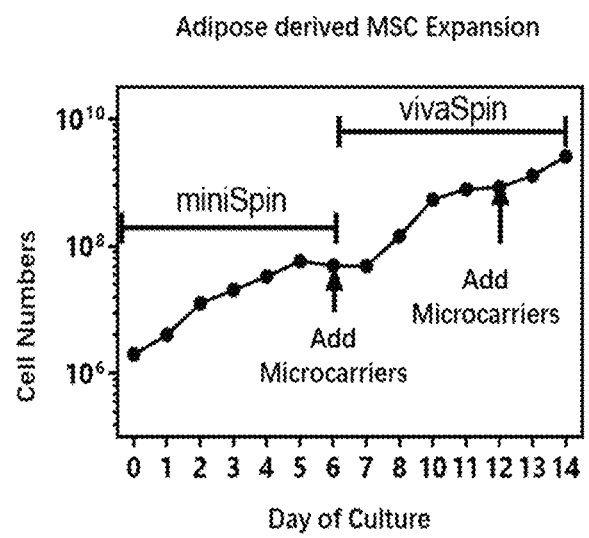
FIG. 32 shows the statistical results of the growth of cell numbers in the first part of Example 7 of the present invention.

The results of the cell number assay are shown in FIG. 32. The entire culture process was maintained for a total of 14 days, from 2 million cells directly inoculated into 10 tablets of Microcarriers™ in the 3D FloTrix® miniSpin's cell culture flask with built-in impeller for 6 days, to the addition of new Microcarriers™ and expanded into the 3D FloTrix® viviSpin automated bioreactor for further culture of 8 days to reach a final harvest of 100 million cells, of which Day 0 to Day 6 in a small-scale bioreactor, after 6 days of culture, 49.2 million cells were harvested from an initial 2 million, representing an approximate 24.6-fold increase in proliferation; a total of approximately 2590 million cells were harvested after 8 days of culture in the automated bioreactor using them as seeds, representing an approximate 52.7-fold increase in proliferation; i.e. a total of approximately 1,295-fold expansion in 14 days of culture.

Figure 34:
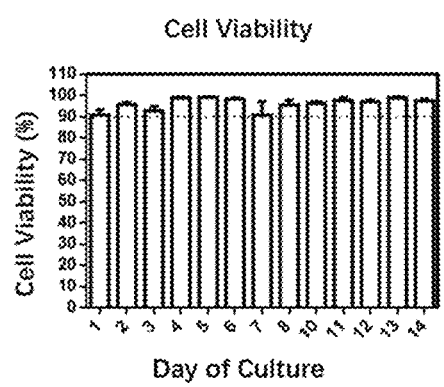
FIG. 34 shows the results of the cellular activity in the first part of Example 7 of the present invention.

The results of the cell activity assay are shown in FIG. 34. The results showed that the cell activity was maintained at over 90% throughout the entire culture process. The entire culture process was carried out requiring only one person, less than 0.25 m$^2$ of space, 14 days of culture time, 2 liters of culture medium and 110 tablets of microcarriers, resulting in significant savings in human, material and financial resources.

II. Continuous Cell Expansion in 3D FloTrix® vivaSpin Bioreactor (1000 mL)
1. 40 tablets of 3D TableTrix™ microcarriers were added to a sterile 3D FloTrix® vivaSpin bioreactor along with a resuspension of 40 mL of 6.6 million adipose-derived MSC suspension on a sterile working bench.
2. The bioreactor is assembled and the process parameters were set to control as follows: active pumping of 10 ccm of 5% $CO_2$ throughout the process, and a temperature of 37° C. 460 mL of complete medium was actively pumped in at a rate of 10 mL/min at T=0 hour, followed by 500 mL of liquid actively pumped out at a rate of 10 mL/min at T=48 hour. Every 24 hours thereafter, 500 mL of liquid was actively pumped out at a rate of 10 mL/min followed by 500 mL of fresh medium actively pumped into the reactor at a rate of 10 mL/min until 120 hours. After actively pumping out 500 mL of liquid n at 10 mL/min at T=120 hour, 40 tablets of 3D Table Trix™ microcarriers resuspended in 500 mL of fresh medium were actively pumped into the reactor at a rate of 10 mL/min. The stirring rate for T=0 to 120 hour was a constant speed of 60 rpm; for T=120 to 136 hour, the stirring rates were variable speeds in cycles of 60 rpm for 5 minutes and 20 rpm for 20 minutes; for T=136 to 240 hour, the stirring rate was a constant speed of 60 rpm (after 240 hours, the stirring mode was a constant speed of 60 rpm). Cells were sampled and counted daily to obtain data on cell expansion curves, and cell activity was measured.

Figure 35:
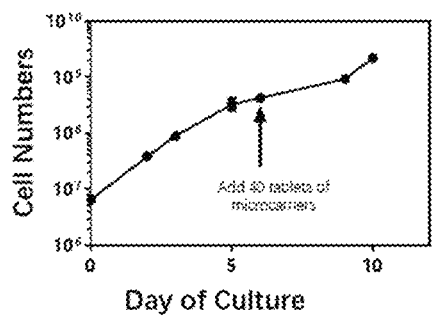
FIG. 35 shows the statistical results of the growth of cell numbers in the second part of Example 7 of the present invention.
Figure 36:
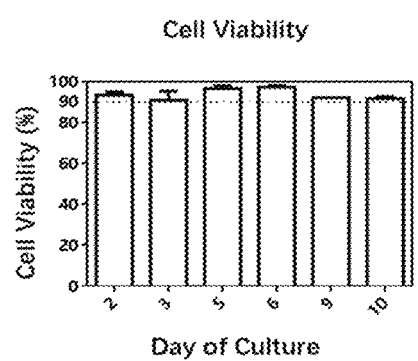
FIG. 36 shows the results of the cellular activity in the second part of Example 7 of the present invention.

The results are shown in FIG. 35 and FIG. 36. The results show that the adipose-derived MSCs were expanded to $2.24 \times 10^9$ cells in the 3D FloTrix® vivaSpin bioreactor from 6.6 million cells inoculated on 40 tablets of microcarriers, with a further 40 tablets of microcarriers (resuspended in medium) pumped in on Day 6 and cultured in full containment for 10 days, achieving an approximate 340-fold expansion. The activity of adipose-derived MSCs in the 3D FloTrix® vivaSpin bioreactor was consistently maintained at over 90%.

III. Partial Characterization of MSC Cultured in Two-Dimensional Flasks and Three-Dimensional Microcarriers Using Flow Cytometric Analysis The microtissues cultured in the steps 1 and 2 were harvested from the cell suspension according to the patent application "A method for Harvesting Cells on Three-dimensional Microcarrier" (Chinese Patent Application No. 201910101736.0), centrifuged at 200×g for 5 minutes, supernatant was discarded, and the microtissues were washed with PBS and evenly divided into 9 centrifuge tubes, which were stained with PE-CD19 (Biolegend, USA, Catalog No.: 302207), APC-CD14 (Biolegend, USA, Catalog No.: 301803), FITC-CD34 (Biolegend, USA, Catalog No.: 343503), APC-CD45 (Biolegend, USA, Catalog No.: 368511), FITC-HLADR (Biolegend, USA, Catalog No.: 307603), FITC-CD90 (Biolegend, USA, Catalog No.: 328107), FITC-CD105 (Biolegend, USA, Catalog No.: 800505), and FITC-CD73 (Biolegend, USA, Catalog No.: 344015) fluorescently labelled antibody, respectively, and a blank buffer as a negative control. After incubation in a refrigerator at 4° C. for 0.5 hours, the cells were washed twice in PBS and resuspended in PBS and transferred to a flow tube. The stained cells were subjected to flow cytometry using a BD FACSAria II flow cytometric sorter, and the expression ratios of the MSC characteristic surface markers were reported by the instrument for cell classification analysis.

TABLE 3

Detection results of cell markers

| Marker/sample | Culture in 2D culture flask | Large-scale culture on 3D microcarrier | Qualification criteria |
|---|---|---|---|
| CD19 | 0.7% | 0.4% | ≤2% |
| CD45 | 0.1% | 0.1% | ≤2% |
| CD14 | 0.2% | 0.1% | ≤2% |
| CD34 | 0.1% | 0.1% | ≤2% |
| HLADR | 0.1% | 0.1% | ≤2% |

TABLE 3-continued

Detection results of cell markers

| Marker/sample | Culture in 2D culture flask | Large-scale culture on 3D microcarrier | Qualification criteria |
|---|---|---|---|
| CD105 | 99.9% | 99.4% | ≥95% |
| CD90 | 99.9% | 99.8% | ≥95% |
| CD73 | 99.9% | 99.9% | ≥95% |

The data showed that MSCs cultured on a large scale on three-dimensional microcarriers had a similar expression profile to those cultured in conventional two-dimension, and both met the qualification criteria.

The above data suggested that the use of three-dimensional microcarriers for the large-scale culture of MSC is feasible, cost effective and can be carried out in closed systems with a high degree of process control and minimal space occupation.

INDUSTRIAL APPLICATION

The present invention provides a set of three-dimensional microcarrier-based cell culture methods, including a three-dimensional microcarrier-based cell recovery method, a three-dimensional microcarrier cell culture-based in situ passaging method, a three-dimensional microcarrier-based method for large-scale expansion of cells, a three-dimensional microcarrier-based in situ cell cryopreservation method, a method of cell attachment culture on three-dimensional microcarrier, a method for harvesting cells on three-dimensional microcarrier and a method for sampling cells cultured on microcarrier.

The three-dimensional microcarrier-based cell recovery method provided by the present invention uses the three-dimensional microcarrier as the substrate, which enables the inoculation of directly recovered cells or microtissues onto a new carrier (microcarrier recovery method), and can then complete the process of cell attachment, adhesion and growth on the microcarrier, avoiding the complex operation of needing to recover cells to a two-dimensional substrate first to grow full and harvest down before inoculating them onto a new culture substrate. As the microcarriers are highly elastic, they cushion the irritation caused by the collision of fragile, newly resuscitated cells with the microcarriers during dynamic incubation and are gentler, and the porous microcarriers have a larger specific surface area providing more space for wall adherence. The porous structure also allows fragile cells to burrow into the pores less susceptible to the shear forces of the flowing medium. The method enables cell passages to be made without interrupting the three-dimensional culture process, thus maintaining the cells in a three-dimensional state throughout the preparation of three-dimensional cultured cell products or tissue engineering products, allowing for fully enclosed cell culture and continuous expansion, with a view to providing some innovation or complement or experience in the field of cell recovery. The advantages of the three-dimensional microcarrier-based cell recovery method: (1) streamlining the process, when the recovered cells are re-cultured in three dimensions, the method eliminates the cumbersome process and the reagent consumables required for the process from single cell collection and cryopreservation after the cells have grown to full size to recovery to two-dimensional culture substrate passaged and digested before inoculation into the microcarrier for three-dimensional culture, which can greatly save time and cost; (2) the obtained cells are close to the in vivo cells, the culture of the cells and subsequent cryopreservation and recovery to re-culture are maintained similar to the in vivo three-dimensional environment, therefore the obtained cells are close to the in vivo cells in terms of physiology and function.

The three-dimensional microcarrier cell culture-based in situ passaging method provided by the present invention inoculates the cultured microcarriers (i.e. seed microcarriers) into new microcarriers to achieve "in situ passaging". The cells can adhere, spread, expand, proliferate and migrate on the three-dimensional microcarrier, and then attach to the new microcarrier by shedding the cells on the seed microcarrier and then proliferate and grow on the new microcarrier, or the new microcarrier and the seed microcarrier come into contact and the cells on the seed microcarrier migrate so that the cells on the seed microcarrier are transferred to the new microcarrier to continue to proliferate and grow, cleverly taking advantage of this to achieve "in situ passaging" of cells on the three-dimensional microcarrier. The advantages of the three-dimensional microcarrier cell culture-based in situ passaging method: (1) it avoids the traditional two-dimensional cell digestion and passaging, which not only reduces the damage to the cells by digestion solution, but also eliminates the tedious operation process of digestion and passaging, thus saving considerable manpower and resources in large-scale culture expansion and obtaining high-quality cells; (2) it is time-saving, it takes time to digest the cells and inoculate them, but the passaging method will save time; (3) the choice of in situ passaging eliminates the need for reagents and consumables such as digestion solution, streamlining the process and reducing costs.

The three-dimensional microcarrier-based in situ cell cryopreservation method provided by the present invention enables in situ cryopreservation of cell culture on three-dimensional microcarriers without the need to separate the cells from the microcarriers and then cryopreserve them, but allows the cells to be directly preserved in situ on the three-dimensional microcarriers. The method enables the cryopreservation of cells without interrupting the three-dimensional culture process, as the microcarriers are not broken or deformed during cryopreservation (−20 to −196° C. until liquid nitrogen preservation) and recovery (i.e. warming and thawing from liquid nitrogen or −80° C.), while the cells remain attached to the three-dimensional microcarriers, thus maintaining the cells in a three-dimensional state throughout the preparation of three-dimensional cultured cell products or tissue engineering products, facilitating the storage, transport and recovery of the expanded three-dimensional cell products by the user. The method is suitable for the long-term preservation of cells cultured on three-dimensional microcarriers with high viability and unchanged cellular properties after recovery.

The method of cell attachment culture on three-dimensional microcarrier provided by the present invention uses a high-density, low-volume method in which the three-dimensional microcarriers are directly swollen using a cell suspension. The cell suspension is absorbed into the microcarrier immediately after addition to the dried three-dimensional microcarrier, facilitating the cells to be drawn directly into the pores of the microcarrier at the time of inoculation, dispersing the cells in the pores of the microcarrier and subsequently adhering for regrowth, providing more growth area for the cells, and on the other hand saving the step that the microcarrier needs to be swollen in advance, thus simplifying the operation of inoculating the cells into the microcarrier. The aseptic operation of the culture is easier and the risk of contamination is avoided. The method is suitable for large-scale bioreactor culture; the unique swelling-absorbing properties of the three-dimensional microcarrier allow a large number of cells to enter the inside of the carrier's connected apertures, better forming a bionic three-dimensional growth pattern and promoting function during in vitro cell culture.

The method for harvesting cells on three-dimensional microcarrier provided by the present invention is directed to harvesting cells on three-dimensional microcarrier. As the cells are cultured on the three-dimensional microcarrier, the present invention enables a gentle harvesting of the cells on the carrier for subsequent applications; the present invention targets the microcarrier for lysis, which dissolves the microcarrier from a solid to a liquid state, thereby releasing the cells on the carrier into a solution, which is separated from the cells by means of centrifugation, thus obtaining the cells. The lysis solution of the present invention is designed for microcarrier and can be tailored to the composition of the microcarrier; the lysis solution lyses the microcarrier and is therefore gentle on the cells, maintains cellular activity and retains the proteins secreted by the cells themselves.

Comparing the method for sampling cells cultured on microcarrier provided by the present invention with the traditional suspension quantitative sampling method, the three samples of cells counted in the microcarrier culture system using the quantitative microcarrier sampling method provided by the present invention are reproducible (small variance) and very close to the actual total.

The three-dimensional microcarrier-based method for large-scale expansion of cells provided by the present invention demonstrates that large-scale culture of MSC using three-dimensional microcarrier is feasible, cost effective and can be carried out in closed systems with a higher degree of process control and minimal space occupation. This will reduce the cost and time of producing cells, allowing cell therapy products to be prepared on a large scale for clinical use.

The present invention is of great importance for the three-dimensional culture of cells, especially stem cells.

The invention claimed is:

1. A three-dimensional culture method for large-scale preparation of stem cells, wherein the method includes a three-dimensional microcarrier-based cell recovery method;
   comprising the step: of inoculating a suspension of cells or cell microtissues onto a three-dimensional microcarrier for cell recovery and culture, optionally, the suspension of cells or cell microtissues is a cell suspension of cryopreserved cells or cryopreserved cell microtissues after thawing,
   wherein the cell culture is performed by cell attachment culture on three-dimensional microcarrier for inoculating cells on a three-dimensional microcarrier, which comprises the following steps: (B1) cell inoculation: mixing a cell suspension with a dried three-dimensional microcarrier to obtain a microcarrier mixed with cell suspension; (B2) cell attachment:
   incubating the microcarrier mixed with cell suspension obtained in the step (B1) so that the cells attach to the three-dimensional microcarrier; (B3) cell culture: after cell attachment in the step (B2), adding a complete culture medium and carrying out culture.

2. The method according to claim 1, wherein the three-dimensional culture method further comprises a method for harvesting cells on three-dimensional microcarrier for separating cells from a three-dimensional microcarrier;

the method for harvesting cells on three-dimensional microcarrier comprises the following steps: (C1) sedimenting by gravity or centrifuging three-dimensional microcarriers attached with cultured cells, removing supernatant to obtain three-dimensional microcarriers containing cells; (C2) adding lysis solution to the three-dimensional microcarriers containing cells, incubating and lysing the three-dimensional microcarriers therein;

(C3) after completely lysing the three-dimensional microcarriers in the step (C2), adding termination solution to terminate the lysis or proceeding directly to step (C4) to terminate the lysis; (C4) centrifuging the system obtained in the step (C3), discarding the supernatant, to harvest cells on the three-dimensional microcarriers.

3. The method according to claim 1, wherein
the three-dimensional microcarrier-based cell recovery method comprises the following steps: (E1) taking three-dimensional microcarriers and placing them in a cell culture vessel, adding cell culture medium and immediately proceeding to the next step or processing for more than 1 minutes; the processing method is standing or stirring; (E2) inoculating a cell suspension obtained by thawing cryopreserved cells or cryopreserved cell microtissues at 37° C. into the cell culture vessel containing microcarriers prepared in (E1), then adding cell culture medium and adjusting a ratio of microcarrier to medium to 1 mg:1 to 1000 μL; placing the cell culture vessel on a stirrer and stirring in an incubator; (E3) after completion of (E2), continuing to stir the cells until cell recovery is completed.

4. The method according to claim 3, wherein
the stirring is constant speed stirring or variable speed alternating stirring or variable speed cyclic stirring; the stirring is clockwise stirring, anticlockwise stirring or stirring in alternating directions; the stirring time is between 0.1 and 100 hours; and the stirring speed is 1 to 200 rpm; or
the stirring is as follows (a) or (b) or (c):
(a) standing for 1 to 4 hours, followed by stirring clockwise at cyclic variable speeds for 1 to 24 hours, followed by stirring clockwise at a constant speed until the 96th hours;
(b) stirring clockwise at cyclic variable speeds for 1 to 24 hours, followed by stirring clockwise at a constant speed until the 96th hours;
(c) stirring clockwise at a constant speed for 1 to 96 hours.

5. The method according to claim 2, wherein in the method of cell attachment culture on three-dimensional microcarrier, the cell suspension has a density of $1 \times 10^4$ to $1 \times 10^8$ cells/mL; the cell suspension is obtained by resuspending the cells in culture medium or liquid biological matrix material; a ratio of volume of the cell suspension to mass of the three-dimensional microcarrier is 1 to 1000 μL:1 mg; incubation conditions are as follows: a temperature of 35 to 40° €40° C., a period of 0.5 to 24 hours; a percentage concentration of carbon dioxide by volume of 5 to 30%; and the attachment method comprises gravity attachment method, swelling attachment method, stirrer rotary attachment method, centrifugal method, surface acoustic wave method or magnetic attachment method.

6. The method according to claim 2, wherein in the method for harvesting cells on three-dimensional microcarrier, a ratio of the mass of three-dimensional microcarrier for attaching and culturing cells to the volume of lysis solution is 1 mg:0.01 to 5 mL; the incubation is at a temperature of ° C. to 40° C. for a period of 10 seconds to 24 hours; a ratio of the mass of three-dimensional microcarrier for attaching and culturing cells to the volume of lysis solution is 1 mg:0.01 to 5 mL; in the step (C4), the centrifugation is at a speed of 50 to 1610×g for a time of 1 to 10 minutes.

7. A method for sampling and counting cells cultured on microcarrier, wherein the method comprises the following steps: (D1) weighing a certain weight of microcarriers for cell culture, placing them in a sampling tube, adding liquid to simulate cell culture process, soaking them at 4 to 60° C. for 0.5 to 24 hours and then marking a scale corresponding to a volume occupied by the microcarriers on the sampling tube as a standard scale; (D2) sampling cells cultured on the microcarrier as follows: sampling the microcarriers from the cell culture system with the sampling tube to bring volume of the microcarriers to the standard scale; (D3) counting the cells in the microcarriers collected in (D2);

(D4) calculating the total number of cells in the entire cell culture system based on the weight of microcarriers weighed in (D1), the number of cells counted in (D3) and the total weight of microcarriers in the entire cell culture system; and thus calculating the cell density.

8. The method according to claim 7, wherein in the step (D1), the liquid added is of the same or similar viscosity, hydrophilicity, pH, ionic concentration as the medium used for cell culture on the microcarrier; in the step (D1), the liquid and the microcarrier is in a ratio of 10 to 1000 μL:1 mg; further comprising sedimentation by gravity or centrifugation after immersion of the microcarriers in the liquid.

9. The method according to claim 1, wherein the method further comprises a three-dimensional microcarrier-based method for large scale expansion of cells in a stirred bioreactor.

10. The method according to claim 6, wherein the three-dimensional microcarriers attached with cultured cells is prepared by a three-dimensional microcarrier cell culture-based in situ passaging method comprises the following steps:

(G1) preparation of a new microcarrier suspension: placing new microcarriers in a cell culture flask with built-in impeller, adding cell culture medium at a ratio of 1 to 2,000 μL:1 mg microcarriers, and standing or stirring for more than 0 hours to obtain the new microcarrier suspension; (G2) preparation of a seed microcarrier suspension: the seed microcarriers have a cell density of 10,000 to 1 million cells/mg microcarriers, resuspending the seed microcarriers to 0.1 to 50 mg/mL with cell culture medium to obtain the seed microcarrier suspension; (G3) inoculation: mixing the seed microcarrier suspension prepared in (G2) into the cell culture flask with built-in impeller containing the new microcarrier suspension prepared in (G1), the ratio of seed microcarrier to new microcarrier is 0.0002 to 200 mg seed microcarriers/mg new microcarriers, adding cell culture medium to adjust the ratio of microcarrier to medium to 1 mg:1 to 1000 μL, placing the cell culture flask with built-in impeller on a stirrer and placing in an incubator for stirring for 0 to 100 hours; (G4) culture: continue stirring to complete the in situ passaging; the stirring speed is 1 to 200 rpm; the stirring is constant speed stirring or variable speed alternating stirring or variable speed cyclic stirring; and the stirring is clockwise stirring, anticlockwise stirring or stirring in alternating directions.

11. The method according to claim 6, wherein the lysis solution comprises an active ingredient for lysing the microcarrier with the elimination of cell attachment;

the active ingredient is selected from an aqueous solution of at least one of collagenase, pepsin, hyaluronidase, dispase, neutral protease, proteinase K, matrix metalloproteinase, sodium citrate, trypsin, deoxyribonuclease, trypsin substitute, protein hydrolase, ethylene diamine tetraacetic acid, lysozyme and glutathione.

12. The method according to claim 6, wherein the termination solution is selected from at least one of whole medium, PBS containing 10% serum albumin or serum, trypsin inhibitor, protease inhibitor, PBS and ionic chelating agent.

13. The method according to claim 1, wherein the three-dimensional microcarrier is a three-dimensional porous microcarrier.

14. The method according to claim 1, wherein the three-dimensional culture method further comprises a three-dimensional microcarrier cell culture-based in situ passaging method, wherein the three-dimensional microcarrier cell culture-based in situ passaging method comprises the following steps: inserting seed microcarriers into new microcarriers; the seed microcarrier is a microcarrier cultured with cells to be passaged.

15. The method according to claim 14, wherein the three-dimensional microcarrier cell culture-based in situ passaging method comprises the following steps:
(G1) preparation of a new microcarrier suspension: placing new microcarriers in a cell culture flask with built-in impeller, adding cell culture medium at a ratio of 1 to 2,000 µL:1 mg microcarriers, and standing or stirring for more than 0 hours to obtain the new microcarrier suspension; (G2) preparation of a seed microcarrier suspension: the seed microcarriers have a cell density of 10,000 to 1 million cells/mg microcarriers, resuspending the seed microcarriers to 0.1 to 50 mg/mL with cell culture medium to obtain the seed microcarrier suspension; (G3) inoculation: mixing the seed microcarrier suspension prepared in (G2) into the cell culture flask with built-in impeller containing the new microcarrier suspension prepared in (G1), the ratio of seed microcarrier to new microcarrier is 0.0002 to 200 mg seed microcarriers/mg new microcarriers, adding cell culture medium to adjust the ratio of microcarrier to medium to 1 mg:1 to 1000 µL, placing the cell culture flask with built-in impeller on a stirrer and placing in an incubator for stirring for 0 to 100 hours; (G4) culture: continue stirring to complete the in situ passaging; the stirring speed is 1 to 200 rpm; the stirring is constant speed stirring or variable speed alternating stirring or variable speed cyclic stirring; and the stirring is clockwise stirring, anticlockwise stirring or stirring in alternating directions.

16. The method according to claim 1, wherein the three-dimensional culture method further comprises a three-dimensional microcarrier-based in situ cell cryopreservation method, wherein the three-dimensional microcarrier-based in situ cell cryopreservation method comprises the following steps:
(A1) centrifuging a three-dimensional microcarrier suspension of cells and discarding supernatant to obtain a cell-containing three-dimensional microcarrier;
(A2) mixing the cell-containing carrier obtained in the step (A1) with a cryopreservation solution and adding to a cryogenic storage tube;
(A3) cooling down the cryogenic storage tube added with the cell-containing carrier in the step (A2) and then transferring it to liquid nitrogen; enabling in situ cryopreservation of cells on three-dimensional microcarrier.

17. The method according to claim 16, wherein in the three-dimensional microcarrier-based in situ cell cryopreservation method,
in the step (A1) the centrifugation is at a speed of 50 to 1610×g for a time of 1 to 10 minutes;
in the step (A2), the ratio of volume of cryopreservation solution to mass of cell-containing carrier is 1 mL: 0.1 to 50 mg; and the cryopreservation solution comprises 10% DMSO, 10 to 90% FBS and 0 to 80% basal medium, 10% DMSO and 0 to 80% basal medium, 10 to 90% FBS and 0 to 80% basal medium or other commercially available cell cryopreservation solutions;
in the step (A3), within 1 to 10 minutes after performing the step (A2), the cryogenic storage tube is placed in a refrigerator and cooled to −20 to −196° C.; the cooling is programmed or non-programmed; the programmed cooling has a cooling rate of −1 to −15° C./min; the cooling time is 1 to 24 hours.

18. The method according to claim 14, wherein the seed microcarrier is prepared by a method of cell attachment culture on three-dimensional microcarrier comprising the following steps:
(B1) cell inoculation: mixing a cell suspension with a dried three-dimensional microcarrier to obtain a microcarrier mixed with cell suspension;
(B2) cell attachment: incubating the microcarrier mixed with cell suspension obtained in the step (B1) so that the cells attach to the three-dimensional microcarrier; and
(B3) cell culture: after cell attachment in the step (B2), adding a complete culture medium and carrying out culture;
wherein the cell suspension has a density of $1\times10^4$ to $1\times10^8$ cells/mL; the cell suspension is obtained by resuspending the cells in culture medium or liquid biological matrix material; a ratio of volume of the cell suspension to mass of the three-dimensional microcarrier is 1 to 1000 µL:1 mg; incubation conditions are as follows: a temperature of 35 to 40° C., a period of 0.5 to 24 hours; a percentage concentration of carbon dioxide by volume of 5 to 30%; and the attachment method comprises gravity attachment method, swelling attachment method, stirrer rotary attachment method, centrifugal method, surface acoustic wave method or magnetic attachment method.

19. The method according to claim 16, wherein the cell-containing three-dimensional microcarrier is prepared by a method of cell attachment culture on three-dimensional microcarrier comprises the following steps:
(B1) cell inoculation: mixing a cell suspension with a dried three-dimensional microcarrier to obtain a microcarrier mixed with cell suspension;
(B2) cell attachment: incubating the microcarrier mixed with cell suspension obtained in the step (B1) so that the cells attach to the three-dimensional microcarrier; and
(B3) cell culture: after cell attachment in the step (B2), adding a complete culture medium and carrying out culture;
wherein the cell suspension has a density of $1\times10^4$ to $1\times10^8$ cells/mL; the cell suspension is obtained by resuspending the cells in culture medium or liquid biological matrix material; a ratio of volume of the cell suspension to mass of the three-dimensional microcarrier is 1 to 1000 µL:1 mg; incubation conditions are as follows: a temperature of 35 to 40° C., a period of 0.5 to 24 hours; a percentage concentration of carbon dioxide by volume of 5 to 30%; and the attachment method comprises gravity attachment method, swelling attachment method, stirrer rotary attachment method, centrifugal method, surface acoustic wave method or magnetic attachment method;

or the cell-containing three-dimensional microcarrier is prepared by a three-dimensional microcarrier cell culture-based in situ passaging method comprises the following steps:

(G1) preparation of a new microcarrier suspension: placing new microcarriers in a cell culture flask with built-in impeller, adding cell culture medium at a ratio of 1 to 2,000 μL:1 mg microcarriers, and standing or stirring for more than 0 hours to obtain the new microcarrier suspension;

(G2) preparation of a seed microcarrier suspension: the seed microcarriers have a cell density of 10,000 to 1 million cells/mg microcarriers, resuspending the seed microcarriers to 0.1 to 50 mg/mL with cell culture medium to obtain the seed microcarrier suspension;

(G3) inoculation: mixing the seed microcarrier suspension prepared in (G2) into the cell culture flask with built-in impeller containing the new microcarrier suspension prepared in (G1), the ratio of seed microcarrier to new microcarrier is 0.0002 to 200 mg seed microcarriers/mg new microcarriers, adding cell culture medium to adjust the ratio of microcarrier to medium to 1 mg:1 to 1000 μL, placing the cell culture flask with built-in impeller on a stirrer and placing in an incubator for stirring for 0 to 100 hours; and (G4) culture: continue stirring to complete the in situ passaging; the stirring speed is 1 to 200 rpm; the stirring is constant speed stirring or variable speed alternating stirring or variable speed cyclic stirring; and the stirring is clockwise stirring, anticlockwise stirring or stirring in alternating directions.

20. The method according to claim 16, wherein the step (A3) is followed by a cell recovery step: the cells are recovered by placing the cryogenic storage tube after the treatment in the step (A3) in a water bath and removing the water bath when the ice in the cryogenic storage tube melts; then diluting the cells by adding 37° C. pre-warmed PBS or basal medium and then centrifuging;

wherein the temperature of water bath can be 35 to 40° C.

* * * * *